(12) United States Patent
Zhou et al.

(10) Patent No.: US 8,323,586 B2
(45) Date of Patent: *Dec. 4, 2012

(54) MICROFLUIDIC CHIPS AND ASSAY SYSTEMS

(75) Inventors: Peng Zhou, Newtown, PA (US); Lincoln C. Young, Ithaca, NY (US)

(73) Assignee: Rheonix, Inc., Ithaca, NY (US)

( * ) Notice: Subject to any disclaimer, the term of this patent is extended or adjusted under 35 U.S.C. 154(b) by 2 days.

This patent is subject to a terminal disclaimer.

(21) Appl. No.: 13/189,787

(22) Filed: Jul. 25, 2011

(65) Prior Publication Data

US 2011/0293489 A1     Dec. 1, 2011

Related U.S. Application Data

(63) Continuation of application No. 11/650,006, filed on Jan. 5, 2007, now Pat. No. 7,959,875, and a continuation of application No. 13/111,137, filed on May 19, 2011.

(60) Provisional application No. 60/760,552, filed on Jan. 19, 2006.

(51) Int. Cl.
*B01L 3/00* (2006.01)
(52) U.S. Cl. ........................................ 422/502; 422/501
(58) Field of Classification Search .................. 422/501, 422/502
See application file for complete search history.

(56) References Cited

U.S. PATENT DOCUMENTS

| | | | |
|---|---|---|---|
| 7,959,875 B2 * | 6/2011 | Zhou et al. | 422/502 |
| 2002/0098122 A1 * | 7/2002 | Singh et al. | 422/100 |
| 2011/0214745 A1 * | 9/2011 | Zhou et al. | 137/2 |

* cited by examiner

*Primary Examiner* — Lore Jarrett
(74) *Attorney, Agent, or Firm* — William Greener; Bond, Schoeneck & King, PLLC

(57) ABSTRACT

The systems and methods described herein include a microfluidic chip having a plurality of microfeatures interconnected to provide a configurable fluid transport system for processing at least one reagent. Inserts are provided to removably interfit into one or more of the microfeatures of the chip, wherein the inserts include sites for interactions with the reagent. As will be seen from the following description, the microfluidic chip and the inserts provide an efficient and accurate approach for conducting parallel assays.

5 Claims, 19 Drawing Sheets

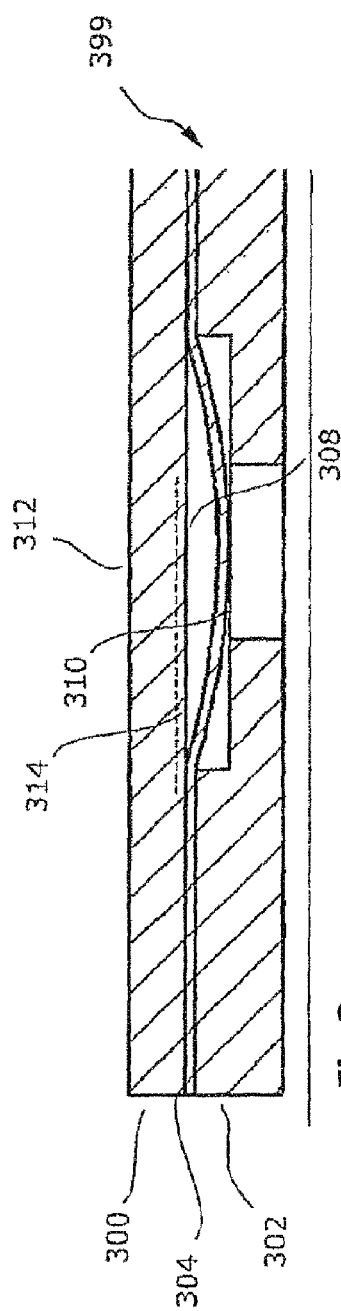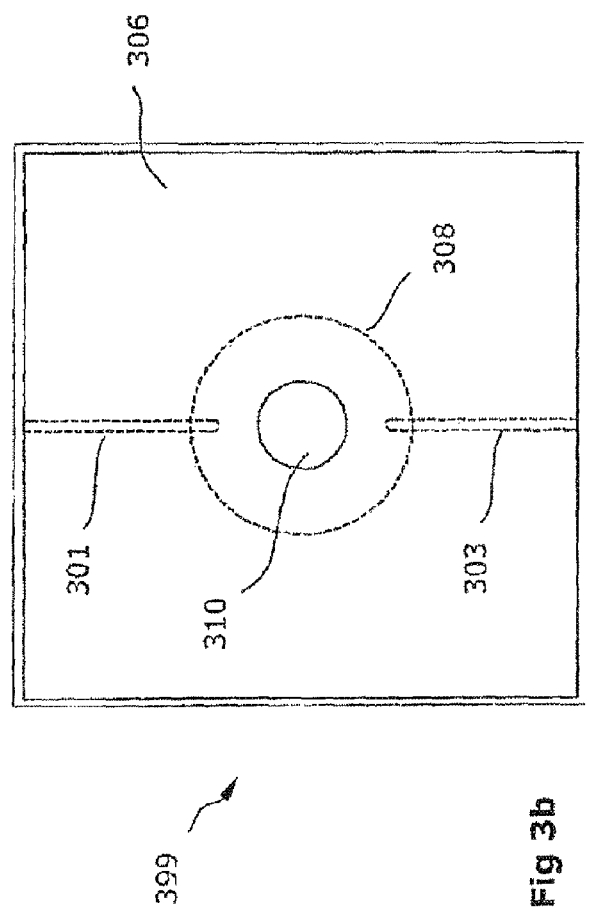
Fig 3a
Fig 3b

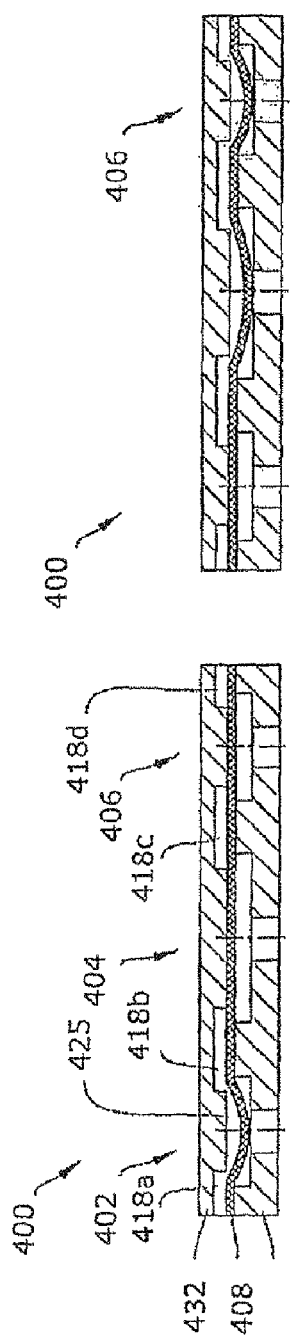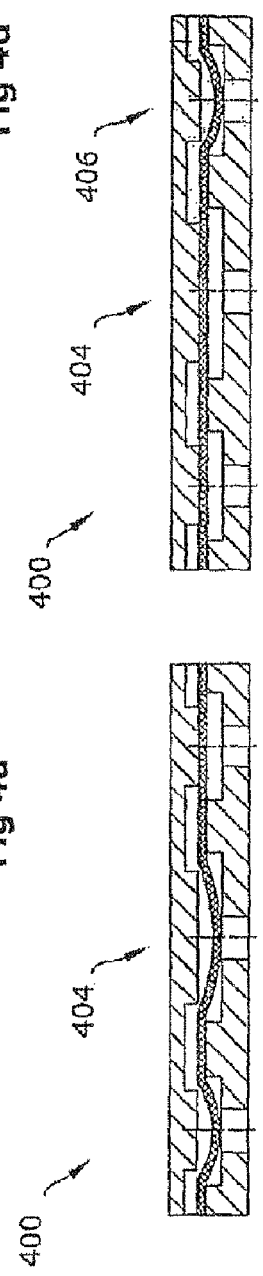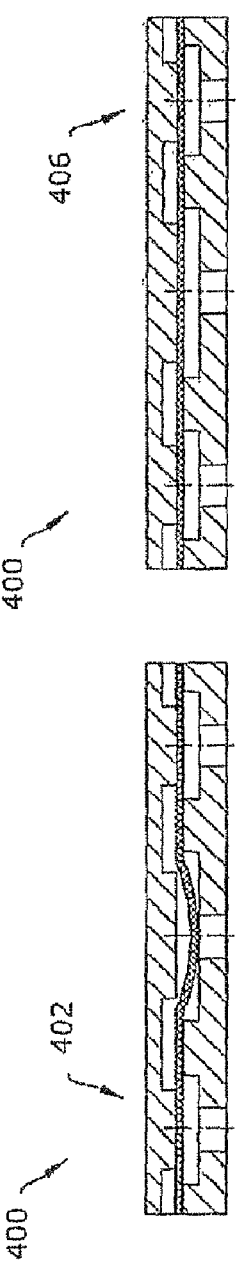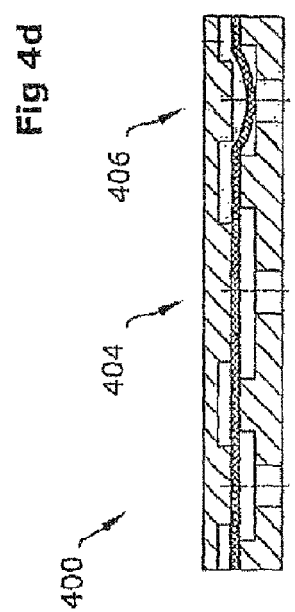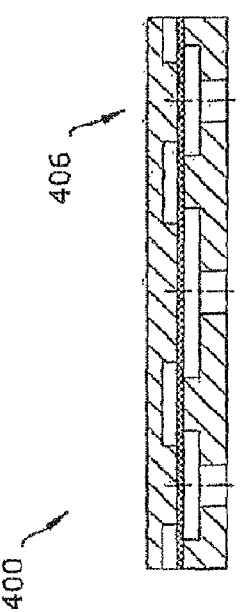

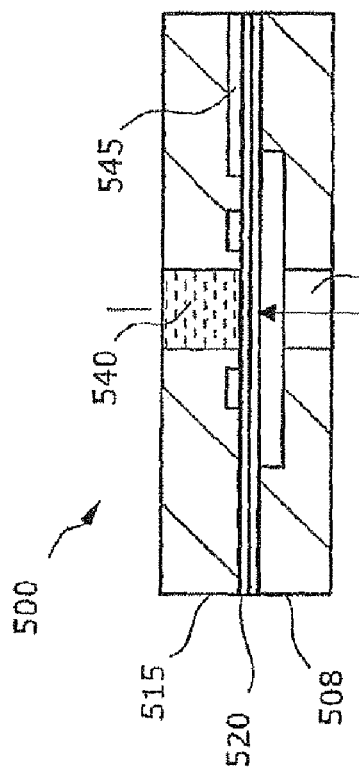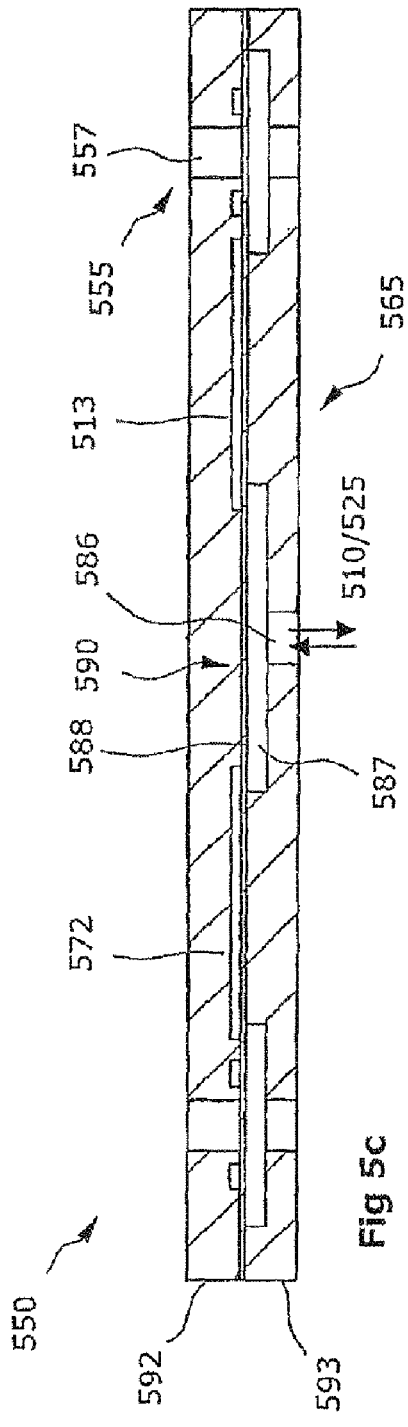

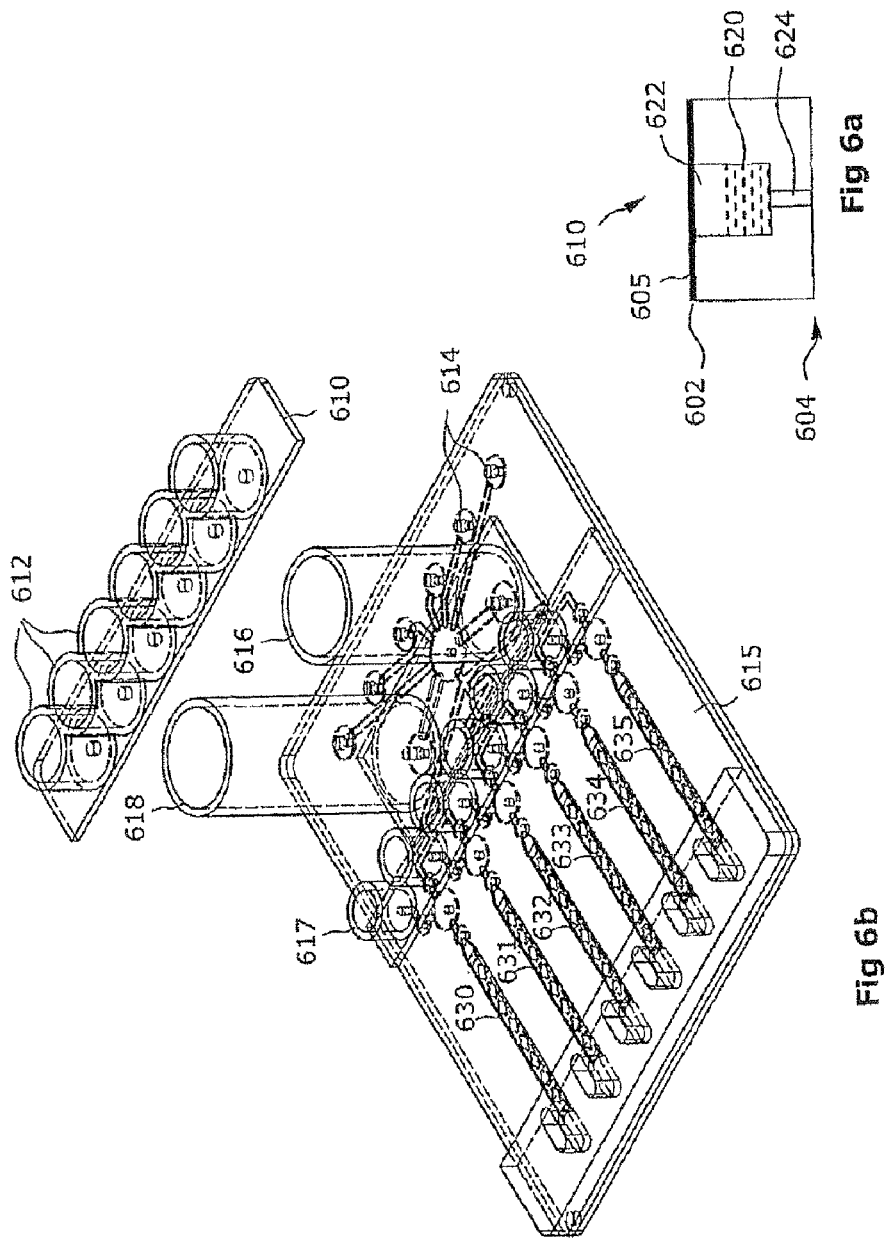

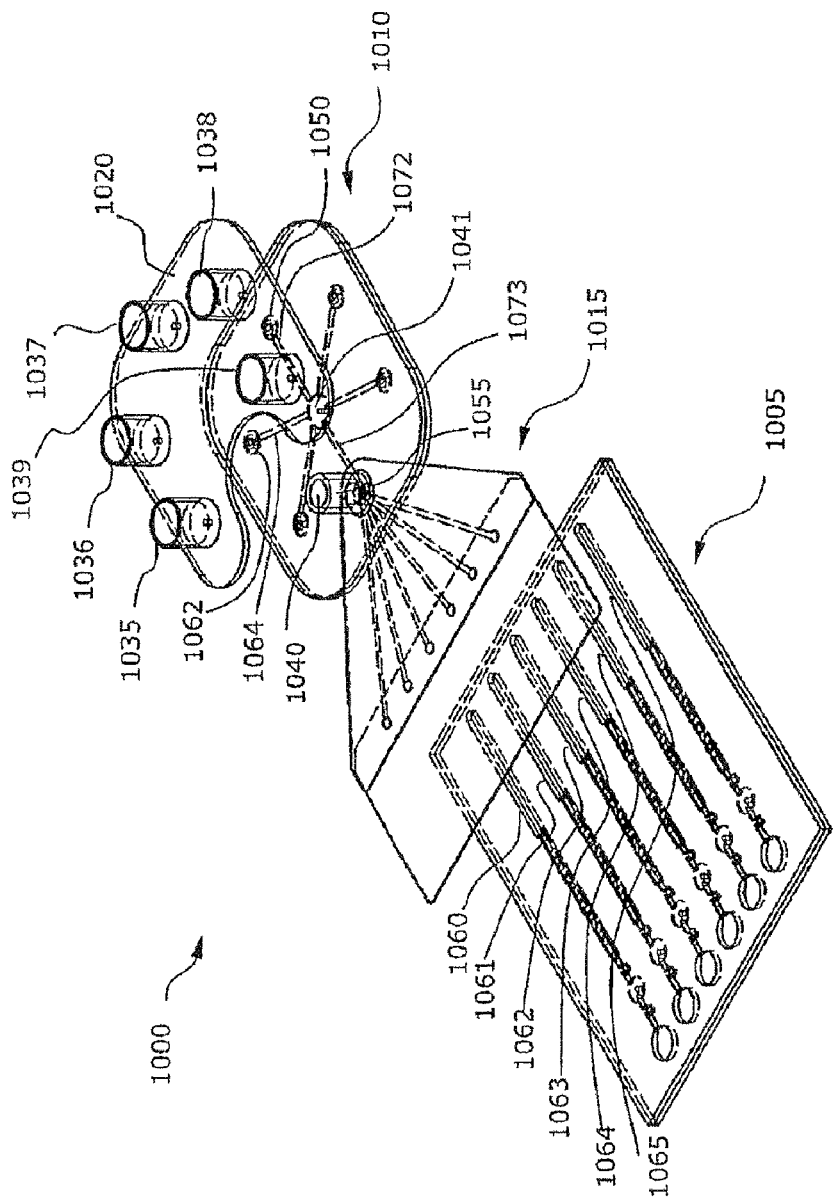

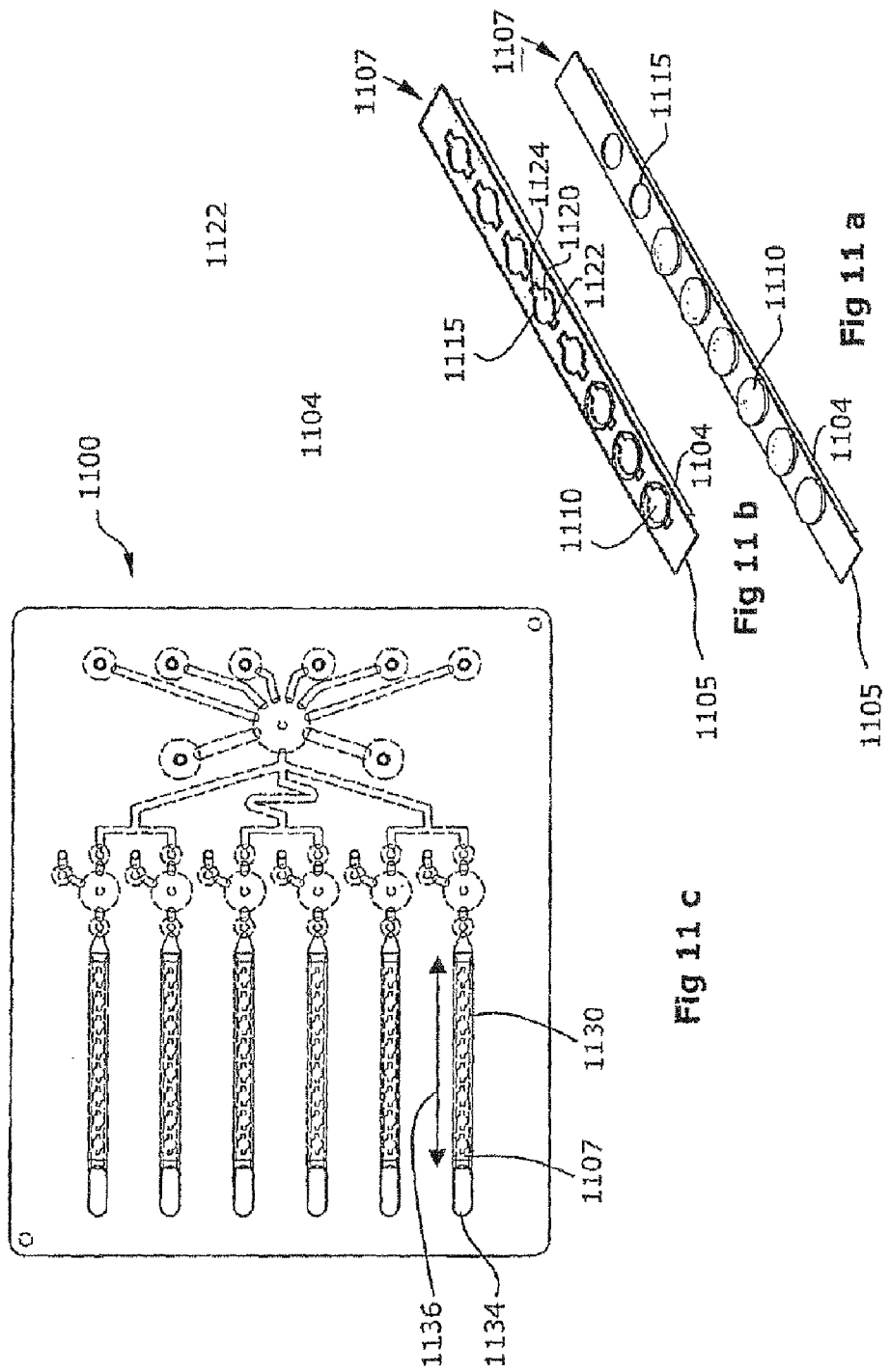

MICROFLUIDIC CHIPS AND ASSAY SYSTEMS

CROSS-REFERENCE TO RELATED APPLICATIONS

This application is a Continuation of U.S. application Ser. No. 11/650,006 filed on Jan. 5, 2007, and of U.S. application Ser. No. 13/111,137 filed on May 19, 2011, which itself is a Divisional of U.S. application Ser. No. 11/650,006, which claims priority to Provisional Application No. 60/760,552, filed on Jan. 19, 2006, and claims priority to all of the foregoing, the subject matter of which is incorporated herein by reference in its entirety.

FIELD OF THE INVENTION

The systems and methods described herein generally pertain to the field of microfluidics. In particular, these systems and methods pertain to microfluidic diaphragm structures, microfluidic chips, portable automated microfluidic reagent processing systems, and fabrication and use thereof.

BACKGROUND AND OBJECTS OF THE INVENTION

"Microfluidics" generally refers to systems, devices, and methods for processing small volumes of fluids. Because microfluidic systems can integrate a wide variety of operations to manipulating fluids, such as chemical or biological samples, these systems have many application areas, such as biological assays (for, e.g., medical diagnoses and drug delivery), biochemical sensors, or life science research in general.

One type of microfluidic device is a microfluidic chip. Microfluidic chips may include micro-scale features (or "microfeatures"), such as channels, valves, pumps, and/or reservoirs for storing fluids, for routing fluids to and from various locations on the chip, and/or for reacting fluidic reagents.

However, existing microfluidic systems lack adequate mechanisms for allowing controlled manipulation of multiple fluids except via prescribed flow patterns, hence limiting the practicality with which the systems can be utilized in various chemical or biological assays. This is because real-world assays often require repetitive manipulation of different reagents under continuously varying conditions.

Moreover, many existing microfluidic devices are restricted for one specific use and cannot be easily adapted or customized for other applications without being completely redesigned. These devices lack modularity, and therefore cannot share common device components that allow one design to perform multiple functions. This lack of flexibility leads to increased production costs as each use requires the production of a different system.

Furthermore, many existing microfluidic systems lack any means for straightforward end-point assays that are able to easily detect interactions or existence of analysts resulting from the assays. By way of example, visual detection of sample color changes after an assay is often used to evaluate the assay results, but this technique is rarely applied in a microfluidic system.

Thus, there exists a need for improved microfluidic systems for processing fluids for analysis of biological or chemical samples. It is desired that the systems are mass producible, inexpensive, and preferably disposable. It is desired that the systems be simple to operate and that many or substantially all of the fluid processing steps be automated. It is desired that the systems be customizable, and be modular such that the system can be easily and rapidly reconfigured to suit various applications. It is desired that the systems be able to provide straightforward and meaningful assay results.

SUMMARY

The system and methods described herein, in one embodiment, include a plastic microfluidic chip configured to process one or more reagents. The chip may comprise various microfluidic features including valves, pumps, channels and reservoirs. The micro-features are interconnected to allow various combinations of fluid flow patterns that can be user specified and tailored to a particular application. In particular, the chip allows for the transport of one or more reagents from respective reagent reservoirs on a reagent cartridge to multiple assay channels via a transport structure. The transport is directed by the automated operation of pneumatically driven pumps and valves. By coordinating the flow of reagent from the reagent reservoirs to the channels both spatially and temporally using the automated methods described herein, a user can efficiently perform biological immunoassays.

In one aspect, the microfluidic chip includes a plastic substrate having a plurality of channels, a distribution structure for introducing a reagent into at least one of the channels, and a configurable transport system for controllably directing a flow of the reagent in the channels.

In one aspect, the channels include a plurality of inlet channels, a plurality of outlet channels and a plurality of assay channels. The configurable transport system comprises a distribution valve connected to the inlet channels and outlet channels for distributing reagents to the assay channels. The assay channels are configured for conducting biological assays.

In one aspect, the inlet channels, outlet channels, assay channels and distribution structure are disposed in the substrate body.

In one aspect, the porting device is a separate reagent cartridge that is detachably coupled to a top surface of the substrate and has a plurality of reagent reservoirs fluidly communicating with the respective inlet channels. The inlet channels are individually valve controlled to deliver reagents from the respective reagent reservoirs to the assay channels through the distribution valve and the outlet channels.

In another aspect, there is a buffer reservoir aligned with an inlet channel to the distribution valve. The buffer reservoir features a substantially larger storage volume than the individual reagent reservoirs for storing a washing buffer. A diaphragm valve located beneath the buffer reservoir controllably releases the washing buffer into the assay channels through the distribution valve.

In another aspect, the invention includes one or more shuttle reservoirs and outlet reservoirs for storing reagents and buffer that are transported during reaction incubation. The shuttle reservoirs are connected to the corresponding outlet reservoirs through respective assay channels. The volumes of a shuttle reservoir and an outlet reservoir are substantially larger than the volume of an assay channel so that a reaction reagent in the assay channel can be transported into the shuttle reservoir and/or the outlet reservoir during reaction incubation.

In another aspect, the invention includes an on-chip waste reservoir aligned with an outlet channel to the distribution valve. The waste reservoir features a substantially larger storage volume than the buffer reservoir for storing all used reagents and washing buffer. An independently actuated diaphragm valve located beneath the waste reservoir regulates fluid flow into the waste reservoir from the shuttle and/or outlet reservoirs via the distribution valve.

In another aspect, the invention includes one or more bi-directional fluidic pumps each coupled to at least three valves respectively controlling a fluid flow through an assay channel, a shuttle reservoir and an outlet channel to the distribution valve. The pump-and-valves structure enables multiple fluid drawing and delivery patterns such as from a reagent reservoir to a shuttle reservoir, from a reagent reservoir to an assay channel to an outlet reservoir, from a shuttle reservoir to an outlet reservoir via an assay channel, from an outlet reservoir to a shuttle reservoir via an assay channel, from an outlet reservoir to a waste reservoir and from a shuttle reservoir to a waste reservoir.

In another aspect, the porting device comprises a separate reagent chip including the inlet channels, the distribution valve and a plurality of reagent reservoirs. The reagent reservoirs are aligned with the inlet channels for introducing reagents to the distribution valve. The porting device also includes a ducting chip having the outlet channels disposed therein. The ducting chip is adapted to detachably couple to the reagent chip and the substrate for introducing the reagents from the reagent chip to the assay channels in the substrate. The separation of an application chip into several modules allows greater design and fabrication flexibility, the utilization of a variety of chip materials and the repetitive usage of the reagent cartridge.

In another aspect, the invention includes an insert disposed in a void volume of an assay channel for conducting biological assays or chemical reactions, wherein the assay channel is configured to receive the insert and prevent a reaction surface of the insert from contacting the channel surface.

In another aspect, the assay channel is adapted to receive the insert from an opening of the outlet reservoir connected to the assay channel.

In another aspect, the void volume of the assay channel includes an opening to the top surface of the substrate wherein the insert can be disposed, and a lid for removably covering the opening of the void volume.

In another aspect, the reaction surface of the insert may include one or more samples analytes or agent for potentially interacting with reagents delivered from the reagent cartridge. The samples analytes or agents are chosen for specific applications. In certain embodiments, the insert includes a perforated membrane film strip and at least one membrane disk coupled to a surface of the membrane film strip and aligned with an aperture on the membrane film strip. The membrane disks are each coated with an agent sample containing a biological and/or chemical material such as a target analyte or analyte-capturing antibodies. In certain embodiments, the apertures include a central circular region and two rectangular regions open to the circular region. The rectangular regions are configured to trap air bubbles in a fluidic flow through the assay channel.

In another aspect, the film strip is made from a non-elastomeric plastic adhesive materials. In certain embodiments, the non-elastomer plastic material includes polymethyl methacrylate, polystyrene, polycarbonate and acrylic. In certain embodiments, the membrane disks are made from nitrocellulose, PVDF and/or nylon.

In another aspect, a heating element is coupled to the microfluidic chip for controlling the assay temperature for enhanced assay repeatability, speed and sensitivity.

In another aspect, the invention provides a method for conducting biological assays. After one or more sample-spotted inserts are disposed into the appropriate assay channels, reagents from the reagent cartridge can be flown through the assay channels via the distribution structure, thereby contacting the reaction surfaces of the inserts. Washing buffer from the buffer reservoir may also be flown through the assay channels to contact the inserts in the channels. During a reaction incubation period or a washing period, excessive reaction reagents and/or washing buffer in the assay channels are pumped back and forth between a shuttle reservoir and an outlet reservoir connected to each assay channel. At the conclusion of the assays, fluidic wastes stored in the shuttle reservoirs and the outlet reservoirs are pumped into the waste reservoir via the distribution structure. By flowing appropriate reagents, including buffers, washing reagents, antibodies, antigens, enzyme conjugates and their substrates, the microfluidic chip can be used to perform an immunoassay or other biological assay on each membrane disk in order to detect the target analytes.

In another aspect, the shuttle reservoirs are used as reagent reservoirs for creating individual assay conditions in each assay channel. Unlike a reagent delivered from the reagent reservoir that creates uniform assay conditions in all assay channels, different reagents or reagents of different concentrations in the shuttle reservoirs may be individually delivered to the assay channels for performing parallel, but non-uniform biological assays.

In another aspect, the end result of an assay is detected by color changes on the inserts using an automated image analysis procedure. The procedure involves quantitatively digitizing an array of color-spotted samples in the assay chip and quantitatively determining the color intensity corresponding to each pixel of a sample spot to generate an averaged, or pixilated, value for each sample. The sample color intensity values yield information about the biological samples on corresponding membrane disks. A threshold value may be computed by using negative control samples. The threshold value, the color intensity values, and the various images corresponding to the sample array may be stored and archived for future reference.

In another aspect, the invention allows for porting of a microfluidic chip to a controller capable of driving the pump and valve structures on the chip. The controller may be electronically or wirelessly connected to a computer or a Personal Digital Assistant (PDA), such as BlackBerry or Palm Pilot, providing an interface for a user to programmably control the assay reactions on the chip.

The inherently small dimensions of devices achieve a portable microfluidic system. Combined with the programmable control directing flow of several reagents through several microchannels into several outlet reservoirs, this invention provides a framework for offering portable "Point-of-Care" (POC) systems with automated assay processing that can be run by users with little training.

In one aspect, the microfluidic chips of this invention are made entirely from plastic materials. In one embodiment, an entire microfluidic chip suitable for portable immunoassay is made from polystyrene, which results in extremely low fabrication costs. An enabler for the use of polystyrene in such an application while preserving the integrity and reliability of the microfeatures disposed therein is the use of weak solvent bonding. These aspects of the technology are described in U.S. patent application Ser. No. 11/242,694, incorporated by reference herein in its entirety.

BRIEF DESCRIPTION OF THE DRAWINGS

These and other features and advantages will be more fully understood by the following illustrative description with reference to the appended drawings, in which the drawings may not be drawn to scale.

FIGS. 3a-b illustrate a microfluidic valve used in the embodiment shown in FIG. 1.

FIGS. 4a-4f illustrate a microfluidic pump used in the embodiment shown in FIG. 1.

FIGS. 5a-c illustrate an inlet valve used in the embodiment shown in FIG. 1.

FIGS. 6a-b illustrate a cartridge and a reservoir used in the embodiment shown in FIG. 1.

FIGS. 8-10 illustrate steps for manufacturing the device of FIG. 7.

FIGS. 11a-c illustrate an exemplary insert sized and shaped to inter-fit within the embodiment shown in FIG. 1.

DETAILED DESCRIPTION OF ILLUSTRATIVE EMBODIMENTS

The invention, in various embodiments, provides microfluidic chips, systems and methods. The following detailed description refers to the accompanying drawings. The following detailed description does not limit the invention. Instead, the scope of the invention is at least the scope defined by the appended claims and equivalents.

Figure 1:
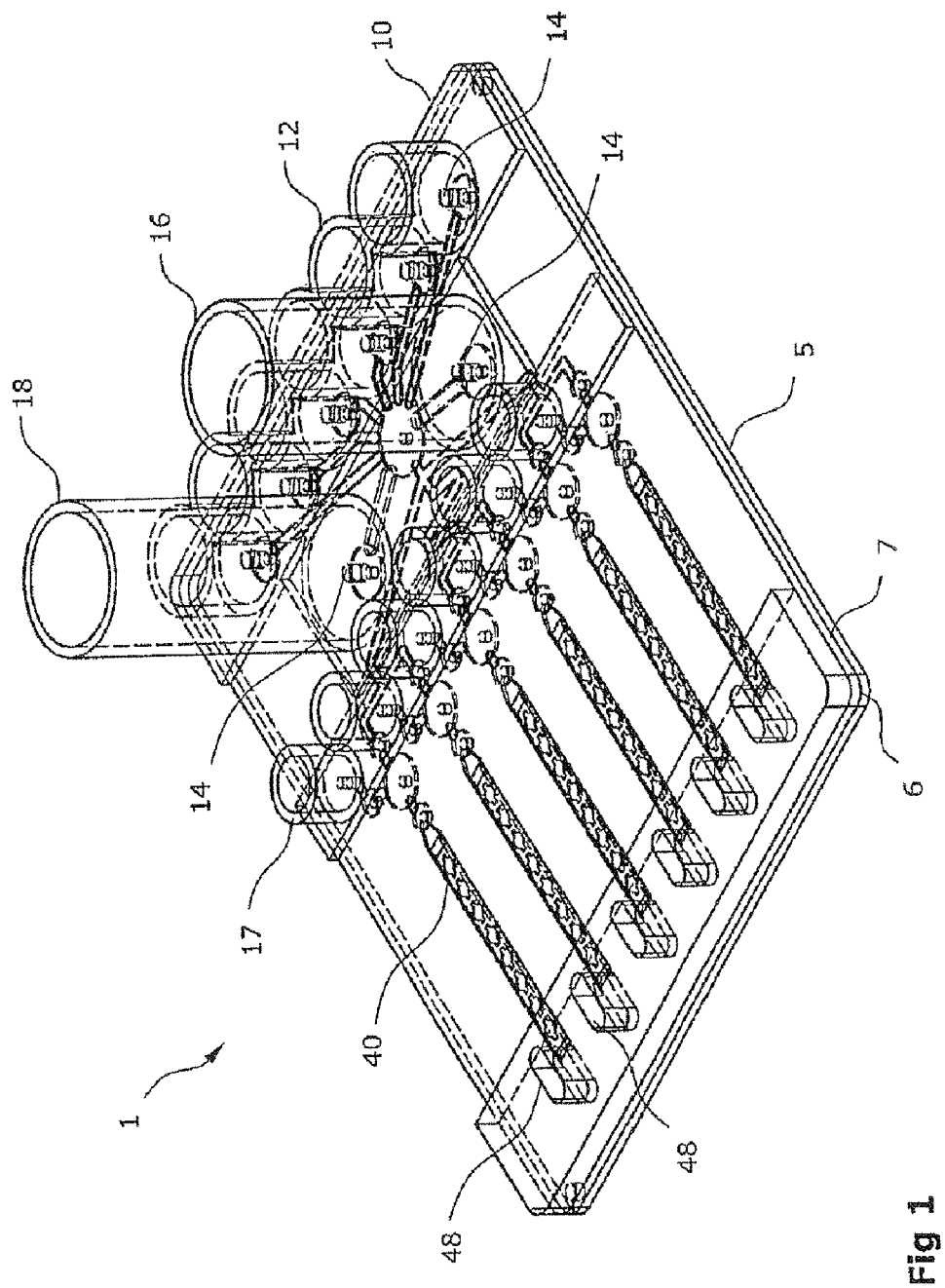
FIG. 1 illustrates one embodiment of a microfluidic chip of the invention.

FIG. 1 illustrates a microfluidic system 1 that includes an assay chip 5 and a cartridge 10 disposed on the chip 5 along a width of the chip 5. The cartridge 10 includes a plurality of reagent reservoirs 12 having side walls that define chambers to hold fluid reagents. The chip 5 includes a buffer reservoir 16 having a cylindrical sidewall to hold a washing buffer, a plurality of shuttle reservoirs 17 adapted to hold reagents during an assay operation, and a waste reservoir 18 adapted to hold used reagents and used buffer after the assay operation. The chip 5 also includes a plurality of inlet valves 14 positioned to align with the various reservoirs. The inlet valves 14 serve to control fluid flows between the reservoirs and respective microchannels in the chip 5.

Figure 2:
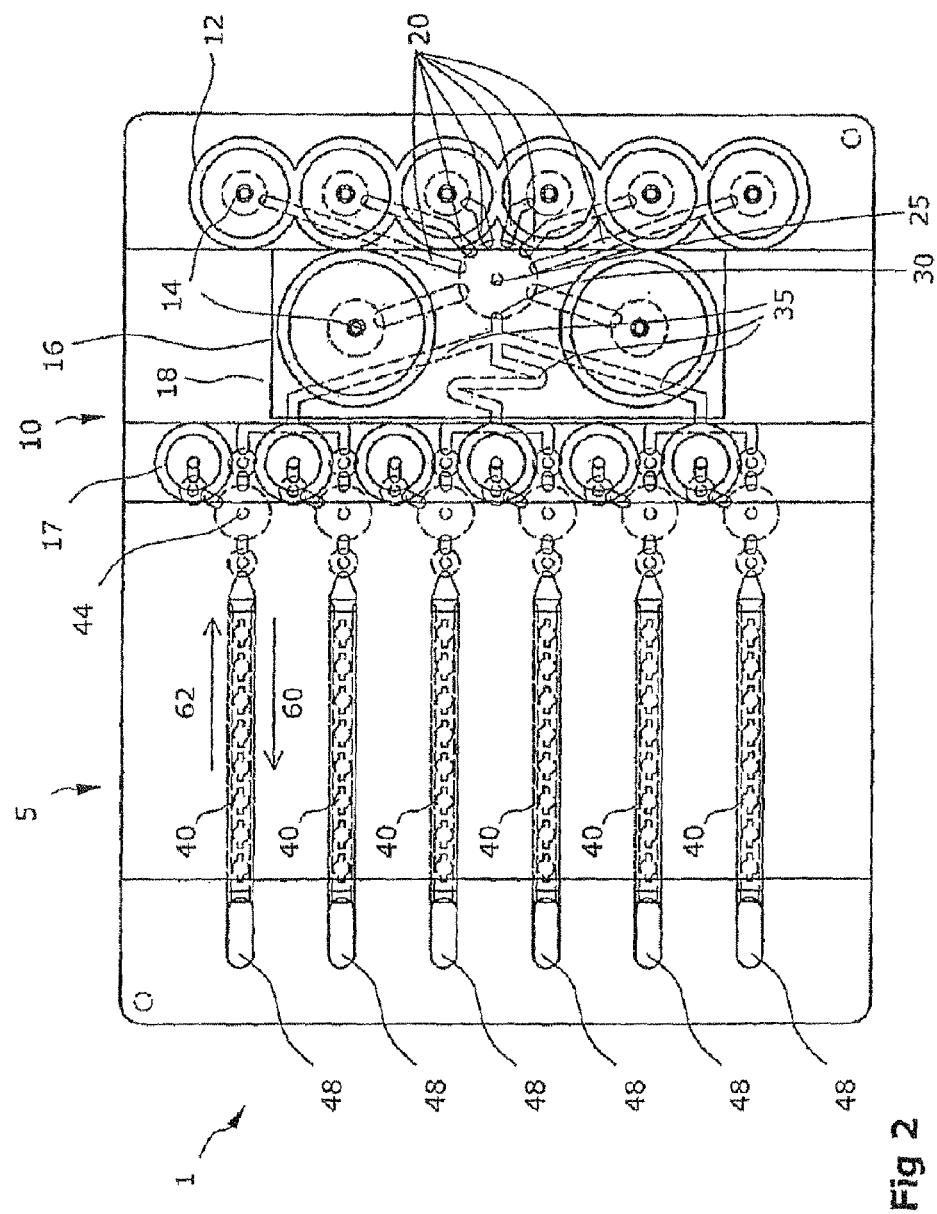
FIG. 2 illustrates an alternative view of the microfluidic chip of FIG. 1.

As illustrated in FIG. 2, the chip 5 includes a plurality of inlet channels 20, a distribution valve 25, an inlet 30, a waste channel 38, a plurality of reagent and or buffer outlet channels 35, assay channels 40, fluid pumps 44, and outlet reservoirs 48. The distribution valve 25 controls the release of fluid from the inlet channels 20 to the inlet 30. The distribution valve 25 controls the release of fluid from the inlet 30 to the waste channel 38. The inlet 30 serves as an inlet to outlet channels 35 which are in fluidic communication with the assay channels 40. The pumps 44 pump fluid in a direction 60 towards the outlet reservoirs 48, but can also be programmed to pump fluid generally in the direction 62 towards the shuttle reservoirs 17 and the inlet 30.

As shown in FIG. 1, the chip 5 is generally constructed from a first substrate 6, a second substrate 7, and a membrane 8 (not shown) disposed in between the two substrates 6 and 7. The membrane 8 has a thickness of between about 10 μm and about 150 μm, or between about 15 μm and about 75 μm. The depicted first substrate 6 and second substrate 7 each has a thickness substantially larger than the thickness of the membrane 8, but in other implementations, has a thickness similar to or less than the thickness of the membrane 8. The microfluidic channels 20, 25, 38, and 40 may be of any suitable dimension, but in certain embodiments have cross-sectional dimensions of between about 1 μm and about 500 μm, or between about 1 μm and about 50 μm.

In certain embodiments, the first substrate 6, the second substrate 7, and the membrane 8 are all made of plastic. Exemplary materials include non-elastomeric polymers, such as polymethyl methacrylate, polystyrene, polycarbonate, and acrylic. These materials are beneficial at least in part because they are reasonably rigid, which is suitable for the first substrate 6 and the second substrate 7. Moreover, these materials can be deformable when used in thin layers, which is suitable for the membrane 8 which may deflect towards and away from the first 6 and second 7 substrates.

The system 1 provides automated "many-to-many" reagent dispensing and processing. By selectively operating inlet valves 14, distribution valve 25 and fluid pumps 44, various combinations of fluid flow patterns among reagent reservoirs 12, buffer reservoir 16, waste reservoir 18, shuttle reservoirs 17 and outlet reservoirs 48 can be achieved. In particular, the distribution valve 25 may be constructed in accordance with the valve structure described with respect to FIGS. 3a-b. FIGS. 3a-b show a three-layer active planar valve structure 399, which may be formed using acetonitrile assisted bonding. The valve structure 399 includes a first substrate 300 having interdisposed microchannels 301 and 303. A membrane layer 304 is selectively bonded to the first substrate 300 in areas 306, thus creating a diaphragm structure 308. A second substrate 302 is bonded to the membrane 304. The second substrate includes a drive chamber 310.

The channel pumps 44 of FIG. 1 may be constructed in accordance with the pump structure described with respect to FIG. 4a-f. A microfluidic pump generally refers to any structure or group of structures capable of applying positive and/or negative pressure to a fluid and/or facilitating the flow of fluid in one or more desired directions. The depicted micro-diaphragm pump 400 generally includes three valves: an inlet valve 402, a drive valve 404 and an outlet valve 406, interconnected by portions 418b and 418c of microchannel 418. In operation, the pump 400 pumps fluid through the microfluidic channel 418 by cycling through six states that are activated sequentially to produce a peristaltic-like pumping effect. Even though FIG. 4 depicts three valve structures 402, 404 and 406 that make up the pump 400, other pump embodiments may contain four or more valve structures.

More particularly, in FIG. 4A, the inlet valve 402 opens and draws fluid from an inlet portion 418a of the microfluidic channel 418 into volume 425 between the membrane 408 and the second substrate 432. In FIG. 4B, the drive valve 404 opens and draws more fluid into the pump system. In FIG. 4C, the inlet valve 402 closes. In FIG. 4D, the outlet valve 406 opens. In FIG. 4E, the drive valve 404 closes, and thereby forces fluid through the outlet valve 406 and into an outlet portion 418d of the microfluidic channel. In FIG. 4F, the outlet valve 406 then closes. These six states complete one pump cycle, displacing a volume of fluid through the pump 400.

The pump 400 is bidirectional. If the cycle is reversed, portion 418d is an inlet portion of the microfluidic channel 418, portion 418a is an outlet portion of the microfluidic channel 418, and fluid flows from portion 418d to portion 418a.

The valve structures 402, 404, and 408 are independently actuatable, in that any one of the valve structures can be actuated with little or substantially no effect on the state of the other valve structures. Those skilled in the art will recognize that alternate sequences of states may produce a pumping effect, and that other pumps can also be used with this invention.

FIGS. 5a-b illustrate an exemplary inlet valve structure 14 of FIG. 1. The valve 14 includes a first substrate 508 with a drive chamber 510 fabricated therein, a second substrate 515 and a membrane 520. A reservoir may be disposed above the second substrate 515 and aligned with reservoir port 540 to provide a source of fluid for porting into channel 545. The reservoirs will be discussed in detail with respect to FIGS. 6a-b. FIG. 5c illustrates an exemplary structure including a plurality of inlet valves 14 of FIG. 1 connected in series.

Various embodiments and alternatives may be applied to the pump and valve structures of this invention. In particular, three or more valves similar to the valve structure 565 in FIG. 5c may be connected in series by microchannels to form a pump that operates with a peristaltic-like mechanism, such as the pumps 44 of FIG. 1. Other arrangements of valve structures interconnected by microchannels can also form generic pumping configurations.

As described above with respect to FIGS. 5a-b, a reservoir may be disposed above the second substrate 515 and aligned with reservoir port 540 to provide a source of fluid for porting into channel 545. This is shown in more detail in FIGS. 6a-b. FIG. 6a shows a cartridge 610 with a top side 602 and a bottom side 604 having a reagent reservoir 612 formed thereon. In particular, the cartridge 610 is provided with its top side 602 and bottom side 604 both sealed by suitable adhesive materials. In the current embodiment, the top adhesive material 605 is a sealing tape, and the bottom sealing material (not shown) may also be a sealing tape. Other suitable adhesive materials may also be used.

FIG. 6a depicts the cartridge 610 having only the reagent reservoirs 612 disposed thereon, although various other cartridge configurations are possible. In one exemplary arrangement, a cartridge includes a buffer reservoir 616, a waste reservoir 618 and a plurality of shuttle reservoirs 617 in addition to the reagent reservoirs 612. In certain implementations, a cartridge includes the reagent 612 and buffer 616 reservoirs. The shuttle 617 and waste 618 reservoirs may be integrally constructed onto the chip 615 or provided on a separate cartridge. In certain implementations, three separate cartridges are provided respectively including the shuttle reservoirs 617, the reagent reservoirs 612, and the buffer 616 and waste 618 reservoirs. In certain implementations, a cartridge has only the shuttle reservoirs 617 for distributing different reagents to assay channels 630-635.

Figure 7:
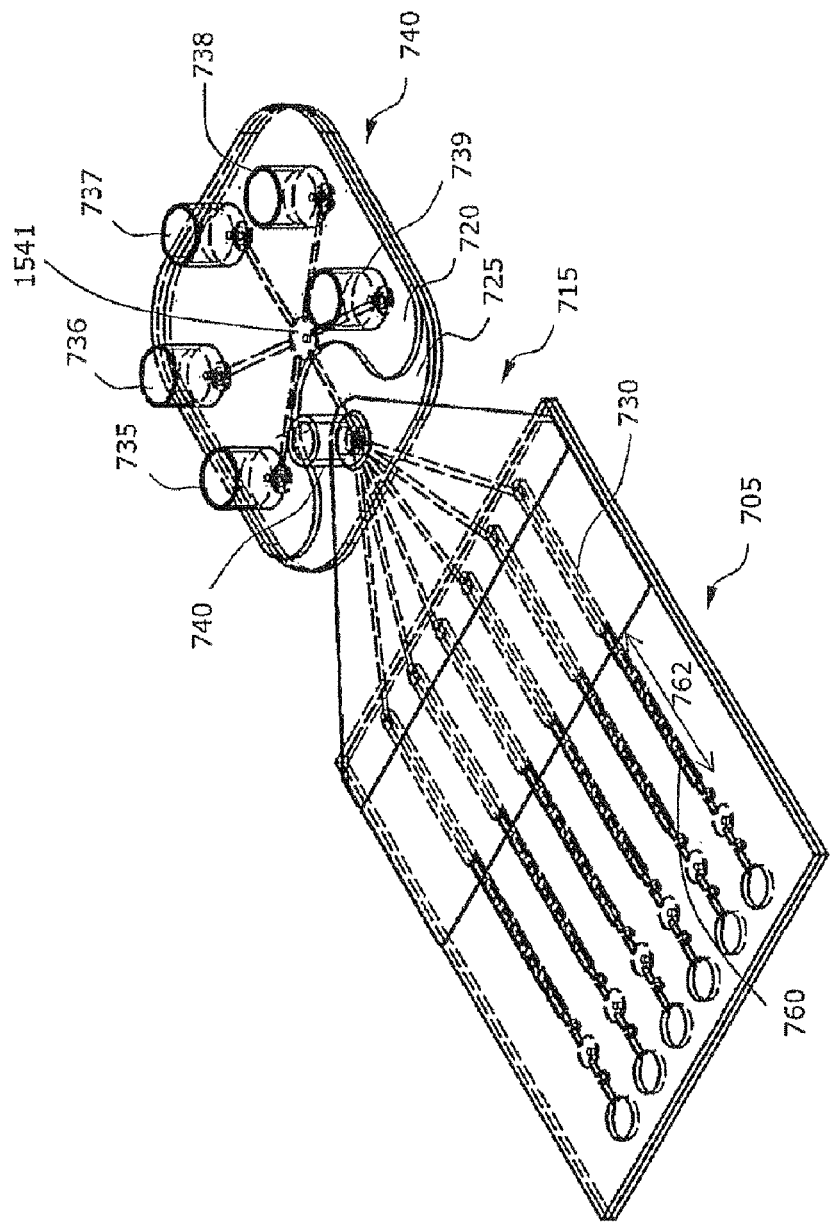
FIG. 7 shows an assay chip having ducts that connect to a separate reagent chip.

FIGS. 7-10 illustrate an alternate method for coupling multiple reservoirs to an assay chip. FIG. 7 shows an assay chip 705, a reagent chip 710, and a ducting chip 715. The reagent chip 710 includes a reagent cartridge 720 and a reagent loading chip 725. The ducting chip 715 serves to provide bi-directional fluid flows between the reagent chip 710 and the assay chip 705. In particular, the reagent chip 710 allows several reagent reservoirs 735-739 to dispense reagents into reservoir 740 before being ported to the assay chip 705 through the ducting chip 715. In certain arrangements, one of the reagent reservoirs 735-739 may be a buffer reservoir for storing a buffer solution. In certain arrangements, one of the reservoirs 735-739 may be a waste reservoir for storing used reagents after an assay.

The ducting chip 715 is rigid enough to provide the necessary structural support to duct the assay chip 705 to the reagent chip 710. However, the ducting chip 715 is deformable such that reagent chip 710 and assay chip 705 need not be exactly aligned along a vertical axis 750 when they are attached by the ducting chip 715.

Figure 8B:
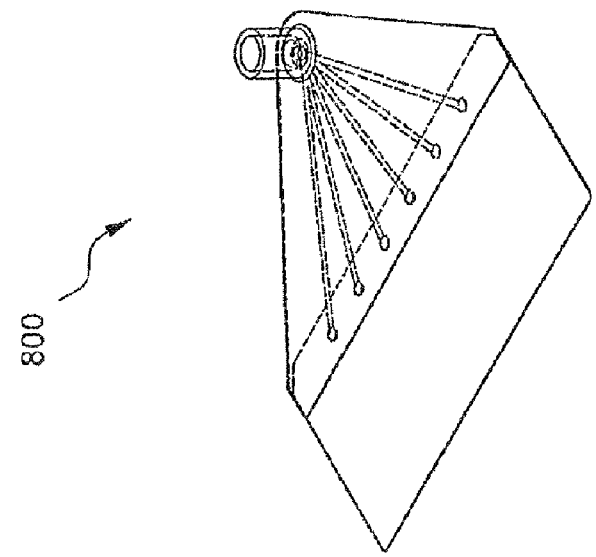
Figure 8A:
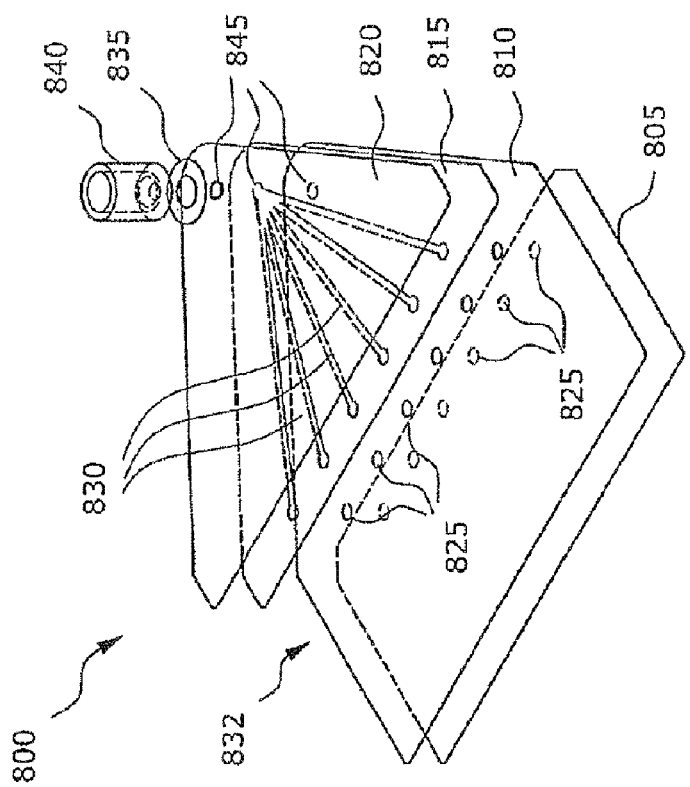

More specifically, according to FIG. 8a, the ducting chip 800 includes a cover layer 805 for being generally disposed over a portion of the channels 730, as shown in FIG. 7. The ducting chip further includes a first support layer 810, a channel layer 815, and a second support layer 820. Layers 805 and 810 are provided with apertures 825 that are aligned to allow fluid to flow from channels 830 in a downward 832 direction. The channel layer includes a plurality of interdisposed channels 830. The first support layer 810, the channel layer 815, and the second support layer 820 include apertures 845 that are substantially aligned to allow fluid to flow in a downward 832 direction from a reservoir 840. An adhesive O-ring 835 adheres the reservoir 840 to the second support layer 820. The layers may be adjoined with the lamination methods described herein. FIG. 8b shows the ducting chip 800 of FIG. 8a after assembly.

Figure 9B:
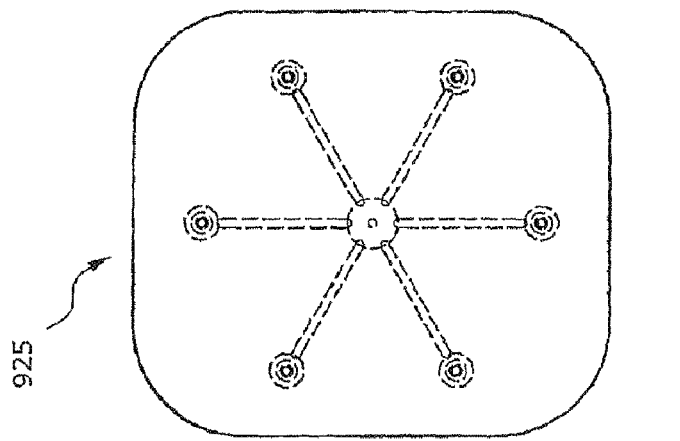
Figure 9A:
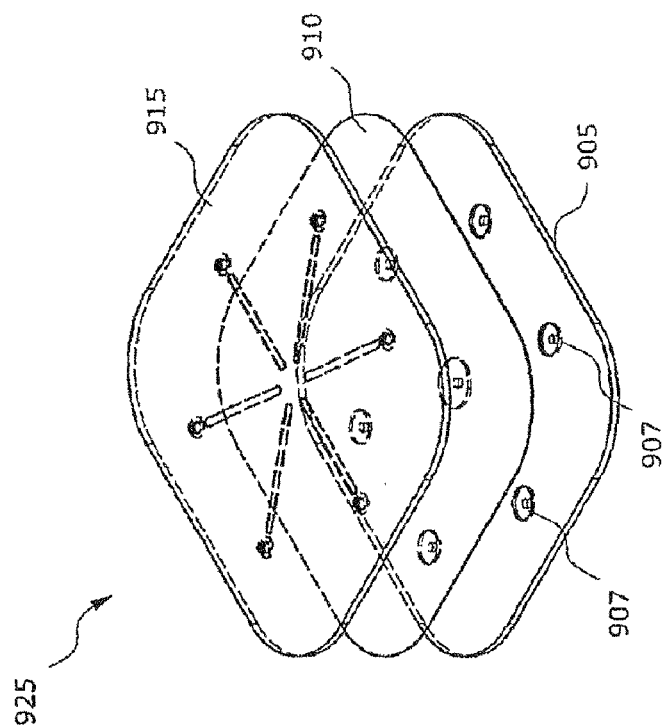

In FIG. 9a, the reagent loading chip 925 includes a bottom substrate layer 905 with drive chambers 907, a membrane layer 910, and a top substrate layer 915 with microchannels etched therein. The layers may be attached with suitable lamination methods described herein. FIG. 9b shows a top view of the reagent loading chip 925.

FIG. 10 illustrates an exploded view of the full structure including the ducting chip 1015, the reagent loading chip 1025, the reagent cartridge 1020, and the assay chip 1005. In particular, FIG. 10 shows the reagent cartridge 1020 being laminated to the reagent loading chip 1025, the ducting chip 1015 being coupled to the reagent loading chip 1025, and the assay chip 1005 being attached to the ducting chip 1015.

Various alternative arrangements may be applied to the microfluidic systems 1 and 1000 of FIGS. 1 and 10, respectively. For example, instead of enclosed assay channels 40 as shown in FIG. 1, a plurality of void regions 1060-1065, as shown in FIG. 10, may be disposed in the respective assay channels. These void regions 1060-1065 may be open to a top surface of the chip 1005. A cover adhesive layer may be disposed over each channel void region 1060-1065.

In another aspect, a temperature-modulating device, such as a heater or a cooler, may be coupled to the microfluidic systems 1 and 1000 to regulate the temperature of the fluids in the systems for providing an optimal environment wherein on-chip biological and/or chemical reactions may occur. In FIG. 1, there are six reagent reservoirs 12, six shuttle reservoirs 17, six outlet reservoirs 48, one waste reservoir 18 and one buffer reservoir 16. In FIG. 10, there are six reagent reservoirs 1035-1039, any of which may be a buffer or waste reservoir. However various other combinations of reagent, shuttle, outlet, waste and buffer reservoirs are possible.

The assay channels may be provided with biological or chemical materials that react with reagents introduced into the microfluidic system. In particular, inserts are provided with chemical and/or biological agents for insertion into the microchannels for the purpose of reacting with the reagents. Exemplary inserts are shown in FIGS. 11a-b. In certain examples, the insert is a flexible plastic strip with an adhesive coating on one side. In certain examples, the insert is a thin polystyrene strip. In certain examples, the insert has a thickness of between about 50 microns to about 500 microns in thickness, a width of between about 1 mm to about 5 mm, and a length of between about 5 mm to about 100 mm. In certain instances, the assay channels are configured accordingly in order to accommodate the inserts disposed therein.

As mentioned above, an insert may be provided with chemical and/or biological agents. In one exemplary implementation, an insert includes a membrane 1104 having adhesive disposed on its surface and membrane disks 1110 adhered to the membrane 1104, wherein the membrane disks 1110 are provided with chemical and/or biological agents. The membrane 1104 is further provided with apertures 1115 over which the membrane disks 1110 lie. The apertures 1115 may be included in a perforated cover strip 1105 adhering to the membrane 1104. The apertures serve to allow fluid contact between the bottom side of the membrane disks 1110 and a fluid flow through channel 1130 wherein the insert 1107 is disposed. In one example of an insert as shown in FIG. 11a, the apertures 1115 are circular. In one example as shown in FIG. 11b, the apertures 1115 each includes a central circular region 1120 with two opposing rectangular regions 1122 open to the circular region 1120. The rectangular regions 122 are oriented on the insert 1107 in a direction 1132 aligned with a direction of fluid flow when the insert 1107 is disposed in the assay channel 1130. This feature enables the insert 1107 to trap air bubbles in the fluid. The membrane disks 1110 are preferred to be circular, although other shapes are possible. The apertures 1115 are shaped and sized to provide structural support for the membrane disks 1110. For the case of circular disks and circular apertures as illustrated in FIG. 11a, the disks 1110 are preferred to have a diameter of between about 1 mm and about 5 mm, and the apertures 1115 are preferred to have a diameter that is between about 5% and about 10% less than the diameter of the disks 1110. For the case of oval-shaped disks and apertures shaped as those in FIG. 11b, a diameter of the central circular regions 1120 of the apertures 1115 may be between about 5% and about 10% less than a major diameter of the membrane disks 1110. A width 1124 of the rectangular regions 1122 may be between about 5% to about 10% less than the diameter of the central circular regions 1120.

The membrane disks 1110 may be made of a porous material such as nitrocellulose. The porosity of the membrane disks 1110 may be sufficiently large to allow fluid and salt passing through but small enough to interact with macromolecules, viruses or bacteria in the fluid. The membrane disks 1110 may be made of nitrocellulose, PVDF and/or nylon, which are suitable materials for use in a microfluidic-based dot-chip process as will be described below. The membrane disks 1110 and the apertures 1115 may be formed by, for example, a die cut or laser cut. The operations of various components of the microfluidic system 1 of FIG. 1 will be described below. By selectively operating the inlet valves 14, distribution valve 25, and channel pumps 44, various combinations of fluid flow patterns might be achieved. In particular, one or more reagents stored in reagent reservoirs 12 and/or washing buffer in buffer reservoir 16 may be selectively dispensed into assay channels 40 at appropriate rates, amounts and temperatures, incubated in the channels 40 and disposed through waste reservoir 18 via outlet reservoirs 48 and shuttle reservoirs 17. Exemplary application of these operations will be discussed herein.

FIGS. 3a-b illustrate one method for operating the distribution valve 25 of FIG. 1. In particular, a positive upward pressure is applied to the diaphragm 308 via the drive chamber 310, the membrane 308 is pushed away against the valve seat 312 between the two microfeatures 301 and 303, effectively preventing any transfer of fluid between them. Alternatively, if a negative downward pressure is applied to the drive chamber 310, the membrane 308 is pulled away from the valve seat 312 and the fluid is free to communicate between the microfeatures 301 and 303 via void region 314. Pressure may be applied through the drive chamber 310 pneumatically or by physically contacting the membrane through the drive chamber 310.

FIGS. 4a-f illustrate one method for pumping fluid through the pump structure 44 of FIG. 1. The method comprises cycling the pump structure through six states that are activated sequentially to produce a pumping effect. In FIG. 4a, the inlet valve 402 is opened and fluid is drawn from inlet microchannel 412 into the volume 402a between the membrane 408 and the first substrate 410. In FIG. 4b, the drive valve 404 is opened, drawing more fluid into the pump system. In FIG. 4c, the inlet valve 402 is closed. In FIG. 4d, the outlet valve 406 is opened. In FIG. 4e, the drive valve 404 is closed, forcing fluid out through the outlet valve 406 into outlet microchannel 418. The outlet valve 406 is then closed. These six states complete one pump cycle, displacing a volume of fluid through the pump. The pump is bi-directional. If the cycle is reversed, microchannel 418 serves as an inlet microchannel, microchannel 412 serves as an outlet microchannel, and fluid may be drawn from inlet microchannel 418 to outlet microchannel 412. Those skilled in the art will recognize that alternate sequences of states may produce other pumping effects.

FIGS. 5a-b illustrate one method for operating the inlet valves 14 of FIG. 1. In particular, a positive pneumatic force 525 is applied through drive chamber 510, forcing the valve 500 to be in a closed position wherein there is no fluidic communication between inlet channel 545 and reservoir port 540. Upon application of a negative pneumatic force 530 through drive chamber 510, the valve 500 is in an open position wherein reservoir port 540 is in fluidic communication with inlet channel 545.

FIG. 5c illustrates the operation of a plurality of inlet valves being connected in series. As depicted, communication between inlet valves 550 and 557 may be controlled by actuating a valve structure 565 connected to the inlet valves. In particular, a positive pneumatic force 570 may be applied through the drive chamber 586 disposed in the bottom substrate 593. This force will push the membrane 588 into conformal contact with a region 590 of the top substrate 592. In this case, the valve is in a closed position with substantially no fluidic communication between adjoining microchannels 572 and 573. A negative pneumatic force 575 applied through the drive chamber 586 will pull the membrane 588 away from the top substrate 592, such that the membrane 588 forms a cavity towards the drive chamber 586 into the region 587. In this case, the valve is in an open position in which adjoining microchannels 572 and 573 are in fluidic communication.

With reference to FIG. 6b, to couple the cartridge 610 to the assay chip 615, a user turns the cartridge 610 such that its bottom side 604 is facing up, removes the bottom sealing backing, aligns the cartridge 610 to the assay chip 615 such that the reagent reservoirs 612 are aligned with respective valves 614, and then presses the assay chip 615 against the cartridge 610. When the reagent cartridge is held together with the assay chip 615, reagent 620 within the respective reagent reservoir 612 is maintained within the reagent reservoir 612 by a hydrophobic property of the surface of aperture 624. Subsequent the chip assembly may be placed on a controller (not shown) and the cover sealing tape is removed to release the reagent 610 onto the assay chip 615 by actuating corresponding valves and pumps described below.

Figure 12:
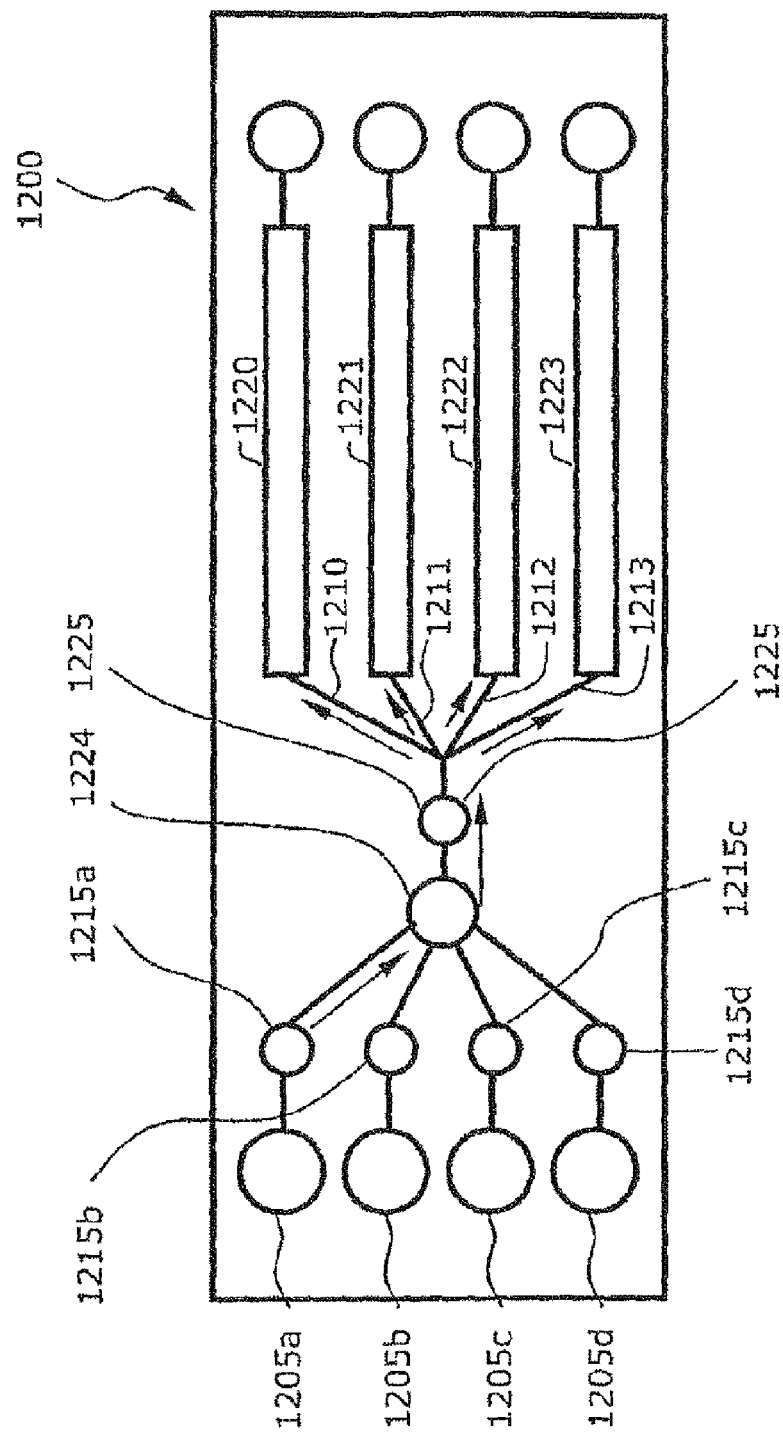
FIG. 12 illustrates an embodiment of a chip in which a single driving force distributes a reagent to a plurality of outlet reservoirs.
Figure 13:
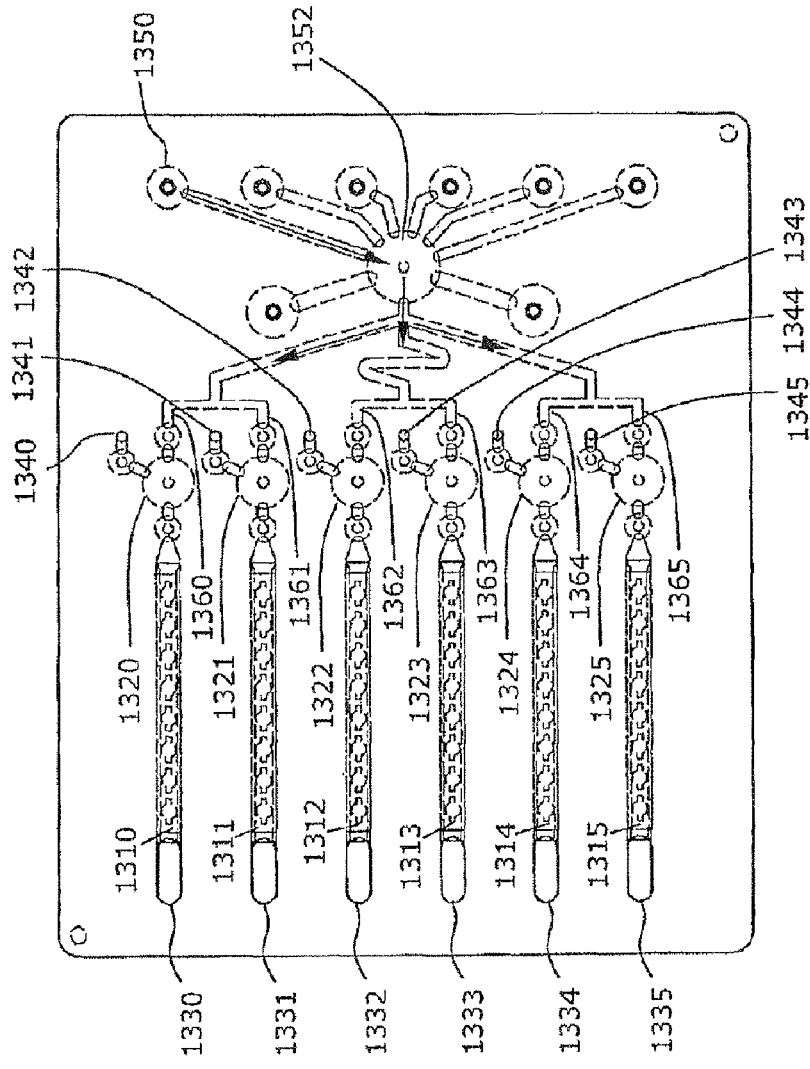
FIG. 13 illustrates an embodiment of a chip in which multiple driving forces distribute a reagent to a plurality of outlet reservoirs.
Figure 14:
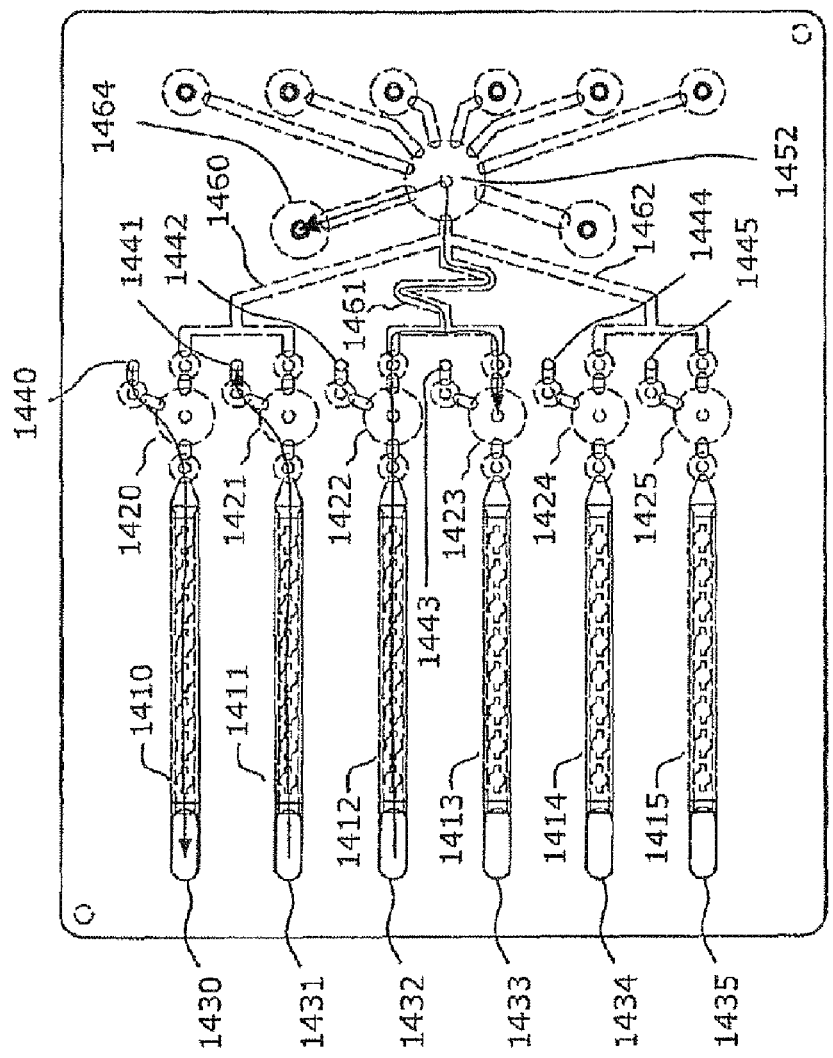
FIG. 14 illustrates an embodiment of a chip having multiple driving forces distributing a plurality of reagents to a plurality of outlet reservoirs.

FIGS. 12-14 illustrate various embodiments for distributing fluids through the chip 1 of FIG. 1 by actuating the pump and valve structures described above. FIG. 12 illustrates a single driving force for distributing a reagent from a reagent reservoir 1205a among a plurality of microchannels 1220-1223 on a chip 1200. The single driving force is produced by an inlet valve 1215a and a drive diaphragm 1224 located in between the area of an inlet valve 1215a and an outlet valve 1225. These three valves may operate according to the peristaltic-like pumping mechanism described above with respect to FIG. 4 to transport fluid contents of reservoir 1205a among the outlet channels 1210-1213. Similarly, reagent contents of reservoirs 1205b-d may be delivered to outlet channels 1210-1213 via pumping action produced by respective ones of inlet valves 1215b-d, drive diaphragm 1224 and outlet valve 1225. This results in a "many-to-many" functionality wherein several reagents are being distributed to several outlet reservoirs.

However, the flow resistances of outlet channels 1210-1213 impact the fluid flow rate on assay channels 1220-1223. In particular, the flow rate in each channel of an assay chip is inversely proportional to the flow resistance of that channel. The outlet channels 1210-1213 may be fabricated to have different flow resistances if an application calls for different channels to have different respective flow rates. However, the sensitivity of flow rates to channel resistance is a detriment to reagent processing if the varying resistances among channels is unintentional. In particular, air bubbles formed during assay may result in varying flow resistances which cause an uneven distribution of reagent across the assay channels 1220-1223.

FIG. 13 illustrates an embodiment of the chip 1 in FIG. 1 that overcomes the variation in flow rates resulting from varying channel flow resistances. Each assay channel 1310-1315 and each outlet channel 1360-1365 are associated with a respective fluid pump 1320-1325. The amount of fluid delivered to the channel by each of the pumps 1320-1325 is relatively unaffected by variations in flow resistance among the assay channels 1310-1315 when the flow resistance is substantially smaller than the pneumatic driving force used to operate the fluid pumps 1320-1325. The channel-to-channel flow rate variation is dominated by the characteristics of pumps 1320-1325 rather than channel flow resistances. FIG. 13 illustrates a reagent from reagent reservoir 1350 being distributed (see arrows) among outlet channels 1360-1365 via distribution valve 1352. In certain embodiments, a plurality of reagents from their respective reagent reservoirs 1350-1355 are delivered to the distribution valve 1352 wherein the reagents may be mixed to create a reagent mixture. In certain embodiments, the reagent or reagent mixture may be further distributed to selected assay channels 1310-1315, outlet reservoirs 1330-1335, and/or shuttle reservoirs 1340-1345.

FIG. 14 illustrates additional fluid distribution patterns of the microfluidic system shown in FIG. 1. In particular, each shuttle reservoir 1440-1445, assay channel 1410-1415 and outlet channel 1460-1462 are connected in series to form a fluid pump 1420-1425, wherein each fluid pump 1420-1425 provides bi-directional fluid flow to and from the respective micro-features. In one implementation, fluid pumps 1420-1425 provides bi-directional fluid flow between shuttle reservoirs 1440-1445 and outlet reservoirs 1430-1435 interconnected by the respective assay channels 1410-1415. In one implementation, a reagent in outlet reservoir 1432 is delivered through outlet channel 1461 and distribution valve 1462 to waste reservoir 1464. In one implementation, a reagent in shuttle reservoir 1443 is delivered to waste reservoir 1464 via outlet channel 1461 and distribution valve 1462. In one embodiment, different reagents or reagents of different concentrations may be introduced to the assay channels 1410-1415 from the corresponding shuttle reservoirs 1440-1445. Introducing reagents from shuttle reservoirs permits variability in assay channel conditions through tailored reagent delivery.

As will be discussed with respect to FIGS. 19-20, the pumps and valves of FIG. 1 may be selectively and programmably actuated. In particular, by selectively actuating certain inlet valves 14, a user may release selected reagents stored in selected reagent reservoirs 12 and/or washing buffer stored in buffer reservoir 16. By selectively actuating channel pumps 44, a user may store these fluids in selected shuttle reservoirs 17 and outlet reservoirs 48, release these fluids stored in the selected shuttle reservoirs 17 and outlet reservoirs 48, and store these fluids in waste reservoir 18. Thus a user is able to perform any desired combination of incubation/mixing/reacting/aspiration of the fluids in the reagent 12 and buffer 16 reservoirs.

The microfluidic system 1000 of FIG. 10 separates the assay functionality of the invention from the reagent delivery functionality. In situations where a particular assay needs to be performed repeatedly, it may be more inconvenient to use a larger cartridge repeatedly than several smaller ones. In one example, the microfluidic system 1000 may be used to run a number of identical assays in parallel. Thus the reagent reservoirs 1035-1039 are provided with enough reagents to run several assays, and the reagent chip 1010 supplies reagent to several chips as their respective assays are being performed. In another example, ducting chip 1015 may be used to duct used reagents from assay chip 1005 into reservoir 1040 on reagent chip 1005. The used reagent in reservoir 1040 is then ported to waste reservoir 1035 for disposal. Waste reservoir 1035 may be utilized to store used reagents from one or more assay chips.

The microfluidic system 1000 operates by flowing fluids from reagent reservoirs 1035-1039 into reservoir 1040. A fluid may be delivered from reservoir 1037 to reservoir 1040 via valve 1041 much like the process shown in FIG. 5c according to which a fluid from valve 550 is delivered toward valve 555 via valve 565. More specifically, actuating valve 1050 delivers fluid into channel 1072, actuating valve 1041 delivers fluid into channel 1073, and actuating valve 1055 delivers fluid into reservoir 1040. In another aspect, a fluid flows from reservoir 1040 into a reagent reservoir 1036 by a similar mechanism as that illustrated in FIG. 5c. For example, with valves 1055, 1041 and 1062 all in open states, actuating valve 1055 pushes fluid into channel 1073, actuating valve 1041 pushes fluid into channel 1064, and actuating valve 1062 pushes fluid into reservoir 1035.

As illustrated in FIG. 11c, to conduct an assay using a microfluidic system 1100 of the invention, the insert 1107 is first deposited into an assay channel 1130 through an opening of the outlet reservoir 1134 that is located at the end of the assay channel 1130 and has a width substantially the same as the width of the assay channel 1130. The insert 1107 is slid into the channel 1130 until it spans a length 1136 of the channel. In certain embodiments as illustrated according to FIG. 7, the insert is inserted into the assay channel 760 through channel void 730. In particular, the channel void 730 is provided with an open top in which the insert is disposed. The insert is slid into the channel 730 until it spans a length 762 of the covered portion of the channel 760. After insertion, an adhesive cover may be placed over the channel void region 730 to form shuttle reservoirs at the end of the assay channel 760.

Figure 15B:
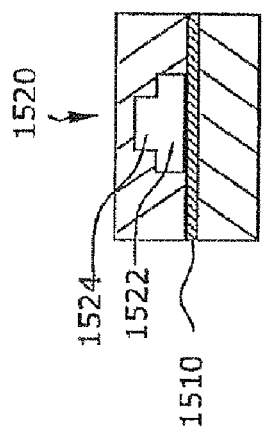
FIGS. 15a-c illustrate a method of inter-fitting the exemplary insert of FIGS. 11a-c within a channel of the embodiment shown in FIG. 1.
Figure 15C:
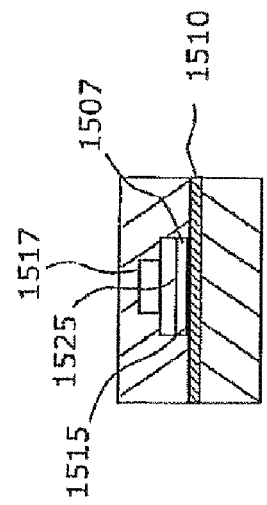
Figure 15A:
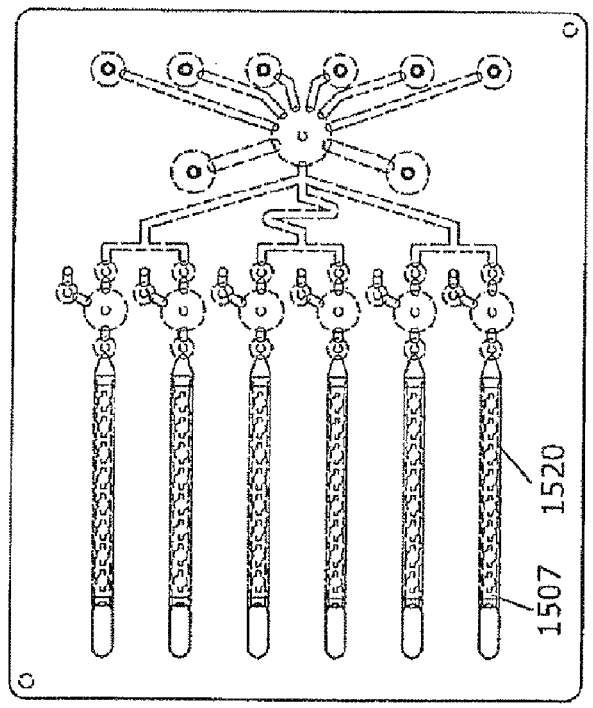

FIG. 15a illustrates the insertion of an insert 1507, and in particular, shows an exemplary channel structure that facilitates the use of the insert 1507. The channel 1520, as shown from a cross-sectional view in FIG. 15b, is a stepped channel including a wide bottom portion 1522 and a narrow top portion 1524. The insert 2017 is inserted into the stepped channel 1520 such that it generally overlies membrane 1510, as shown in FIG. 15c. More specifically, FIG. 15c shows the insert 1507 having an aperture 1515 and a membrane disk 1525. The insert 1507 is situated in the channel 1520 such that the top surface of the membrane disk 1525 does not contact a top surface 1517 of the channel 1520, allowing for fluid in channel 1520 to flow around and contact the membrane disk 1525.

In one aspect, the insert is used to perform an assay similar in principle and function to a dot-ELISA method. The dot-ELISA is a method, known in the art, for detecting the presence of a target analyte within samples. Drawbacks of the conventional dot-ELISA process include difficulties with standardization. Many of the steps are often performed by hand in Petri dishes and the specification of these procedures is vague. Additionally, sample locations are hardly controllable. When sample is spotted on a membrane surface, the hydrophilicity of the material may lead to rapid sample spreading and diffusion. Larger sample amounts result in larger spotted areas. Moreover, since detection sensitivity is related to analyte density per unit area, this diffusion means that larger sample amounts do not necessarily result in lower detection limitation. The present invention employs a similar assay processing, but allows for standardized and more efficient handling, treatment, and analysis. In particular, samples are applied to a membrane disk 1110 as shown in FIGS. 11a-b. The samples are air dried, and then the insert 1105 is disposed in an assay channel of a microfluidic chip, similar to that of FIG. 1.

With reference to FIG. 1, the operation of the microfluidic chip 1 in performing assays will be discussed. Various reagents are stored in reagent reservoirs 12 for conducting on-chip immunoassay. The reagents include fluids that will be employed in a dot-ELISA assay. More specifically, various reservoirs may include one or more of buffer washing buffer, antibody, antibody with conjugated enzyme, and enzyme substrate. In some cases, a buffer reservoir 16 may be used to store a washing buffer. The buffer reservoir 16 may feature a substantially larger void volume than the individual reagent reservoir 12. The reagents are released from their respective reservoirs 12 by activating respective inlet valves 14 and then distributing the reagents throughout the assay channels 40 using the activation of distribution valve 25 and channel pumps 44. The washing buffer in buffer reservoir 16 may also be released into the assay channels 40 in a similar manner. The order and timing of release of the reagents and buffer from their respective reservoirs will correspond to the steps of the assay method used. By way of example, the reagents may correspond to the reagents described above with respect to the immunoassay process, and are released in accordance with the order and timing of the steps mentioned above. The released reagents flow through the assay channels 40 and contact the inserts 70 therein. With respect to FIG. 15c, a fluid flowing through the narrow portion 1524 of the stepped channel 1520 contacts and reacts with agents on the membrane disks 1525. Apertures 1515 provide for the possibility of additional fluid contact along a bottom side of the membrane disks 1525.

As mentioned above, the channels may be provided with materials with which the fluid reagents react, i.e., reagents may flow through assay channels with membrane disks disposed therein, thereby causing the occurrence of interactions between the reagents and the analysts on the membrane disks. It may be desirable to allow dynamic flow conditions or longer incubation times for the reactions via multiple passes of the reaction reagent through channels. This is achieved in part by the bidirectional pumping functionality of this invention. In particular, with reference to FIG. 1, the bidirectional channel pumps 44 are used to repeatedly shuttle a reagent back and forth between the shuttle reservoirs 17 and outlet reservoirs 48 along respective assay channels 40. This cycling action provides multiple passes for much greater efficiency at longer reaction time. The outlet reservoirs 48 and shuttle reservoirs 17 are directly vented to the atmosphere, thereby allowing release of air from the channels 40 during the pumping cycles. In certain examples, the void volume of each shuttle reservoir 17 and each outlet reservoir 48 are substantially larger than the void volume of each assay channel 40 so that reagents in the channels 40 may be stored in the reservoirs during the back and forth pumping action. After the assay operation, used reagents are then transported to the waste reservoir 18 for disposal. In one example, the void volume of waste reservoir 18 is substantially larger than the void volume of the buffer reservoir 16 for storing all used reagents and washing buffer after an assay operation. After the inserts are treated with different reagents, the color of the membrane disks may be observed for the presence of a target analyte in the samples.

The systems described herein bring several new assay advantages to a conventional dot-ELISA format assay. In particular, with reference to FIG. 11, the hydrophobic nature of the insert 1107 along with the inherent surface tension of the liquid sample allows a user to apply a larger amount of sample to a membrane disk 1110 without diffusion or spreading of the sample to other disks 1110 nearby. In one implementation, sample spotting onto the insert 1107 is accomplished by placing the insert 1107 on an absorbent backing material such as a chromatograph paper with membrane disk surface touching the paper. The combination of the water-absorbent ability of the backing material and the sample-retaining ability of the insert 1107 give rise to rapid sample absorption and concentration effects during spotting. Furthermore, the sample droplet diffusion area is substantially defined by the area of the membrane disk 1110. This results in several advantages, such as after a larger amount of sample has dried on the membrane disk, a higher density of sample within the area defined by the membrane disk 1110 is achieved. In addition, since there is less risk of diffusion and contamination of sample material between different membrane disks 1110, the membrane disks 1110 may be placed closer together than the sample spots 2210 would be placed on the monolithic membrane 2205 as shown in FIG. 22, thus resulting in improved space efficiency for on-chip processing and potential reagent savings. Moreover, placing the membrane disks 1110 at predefined and well known locations along the insert 1107, with embedded barcodes or other identifiers on-chip, facilitates the use of the assay chip in automated data processing and image analysis methods that make data archiving for on-chip immunoassay results much more useful.

Figures 16A, 16B:
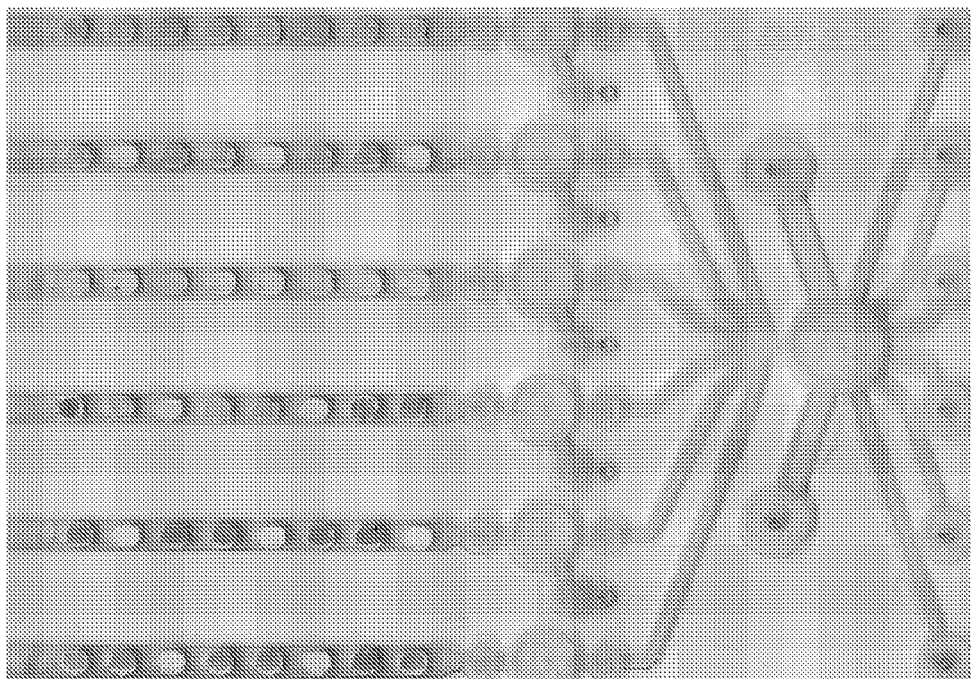
FIGS. 16a-b show the results of a microfluidic-based on-chip immunoassay process.

FIG. 16a illustrates a plurality of inserts 1705 in channels after an assay has been performed. As shown, certain membrane disks 1710a have been colored as positive results by an enzyme-substrate reaction, indicating the presence of a target analyte in a sample disposed on the corresponding membrane disk. Other membrane disks 1710*b* are substantially not colored, indicating no target analyte in a sample disposed on the corresponding membrane disk. In a preferred arrangement, each insert 1705 includes eight membrane disks 1710. Each chip may include six or more assay channels, and therefore at least 48 samples may be assayed simultaneously.

In one implementation, an image analysis method is provided for the automated processing of on-chip immunoassay results. In particular, a microfluidic chip may be scanned utilizing, for example, a photo scanner or a digital camera to capture one or more colored images of the inserts after an assay operation. FIG. 16*a* provides an exemplary image of an 8×6 sample-spotted array. In one embodiment, the scanned images may be stored in a handheld device for further off-line manipulation or sent to a remote computer for off-line image analysis. Image analysis software may then be used to analyze the color intensities of the membrane disks from the captured color images. The intensity of each membrane disk 1710 is subsequently digitized into pixels with a numerical value assigned to each pixel. By averaging the numerical values of the pixels for each membrane disk, one may systematically determine a color intensity value corresponding to the membrane disk 1710. FIG. 16*b* illustrates an exemplary array of color intensity values 1716 corresponding to the membrane disk array shown in FIG. 16*a*.

In one embodiment, each membrane disk 1710 in a sample array is uniquely identifiable by a combination of a barcode embedded in the chip and a set of coordinates specifying the channel and insert positions at which a membrane disk is located. For example, as shown in FIG. 16*a*, a membrane disk 1710*c* on the upper-left corner of a chip that is bar-coded as CHIP-0001 may be labeled as CHIP-0001-A1, where A1 indicates a combination of the column 1712 and row 1714 positions where the disk 1710*c* lies. Hence, placing the membrane disks 1710 at predefined locations on a bar-coded chip enables their corresponding color intensity values 1716 to be easily archived in a database for future reference.

Figure 17:
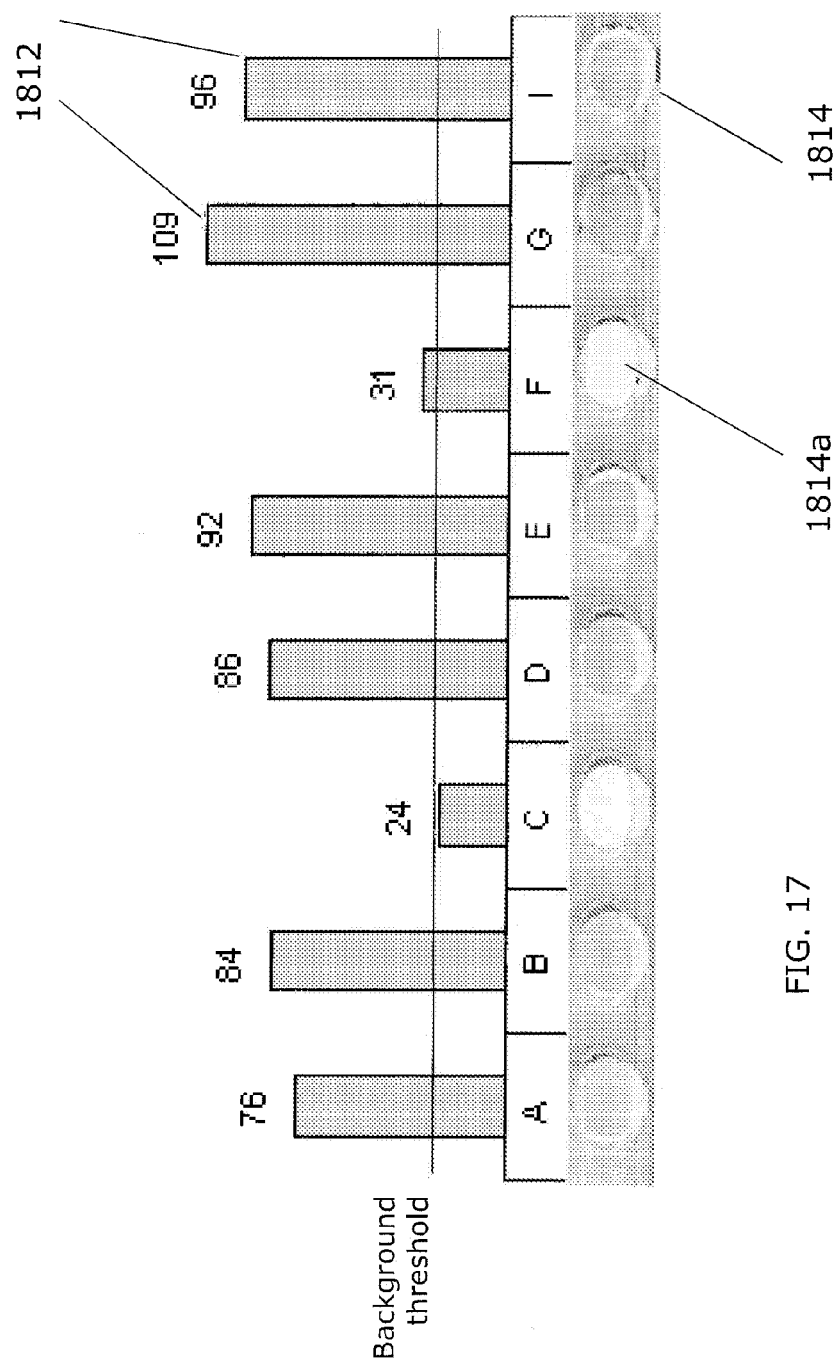
FIG. 17 illustrates steps in identifying samples containing a target analyte.

In one example, a protocol is provided for interpreting a color intensity value 1716 for identifying the presence of a target analyte in a sample disposed on the corresponding membrane disk 1710. According to the protocol, a threshold value is computed using negative control disks such that a color intensity value 1716 is interpreted as having a positive result for target analyte if the color intensity value is above the threshold value. FIG. 17 provides an illustration for determining the presence of a target analyte in eight exemplary samples. These samples are disposed on membrane disks 1814 and correspond to computed color intensity values 1812. The threshold value 1810 in this particular embodiment is 26.8 by arithmetically averaging C1, F1, B2, E2, H2, C3, F3, B5, E5 and H5 as shown in FIG. 16*b*. As shown, the membrane disks 1814 in positions A, B, D, E, G, H are identified as having coated with the target analyte-containing solution. This automated identification procedure reduces human reading errors, especially when interpreting samples, such as that in position F, where the corresponding color intensity 1814*a* is fairly close to the threshold value 1810.

The samples and target analytes for the assay may be any samples and targets suitable for use with immunoassay processes. The samples may include control samples and experimental samples. Experimental samples are generally taken from a subject with a condition of interest, and control samples generally mimic the subject but exclude the analyst of interest. Typically, experimental samples are taken from a potentially diseased patient. A subject may be, for example, a human, animal or plant.

Figure 18:
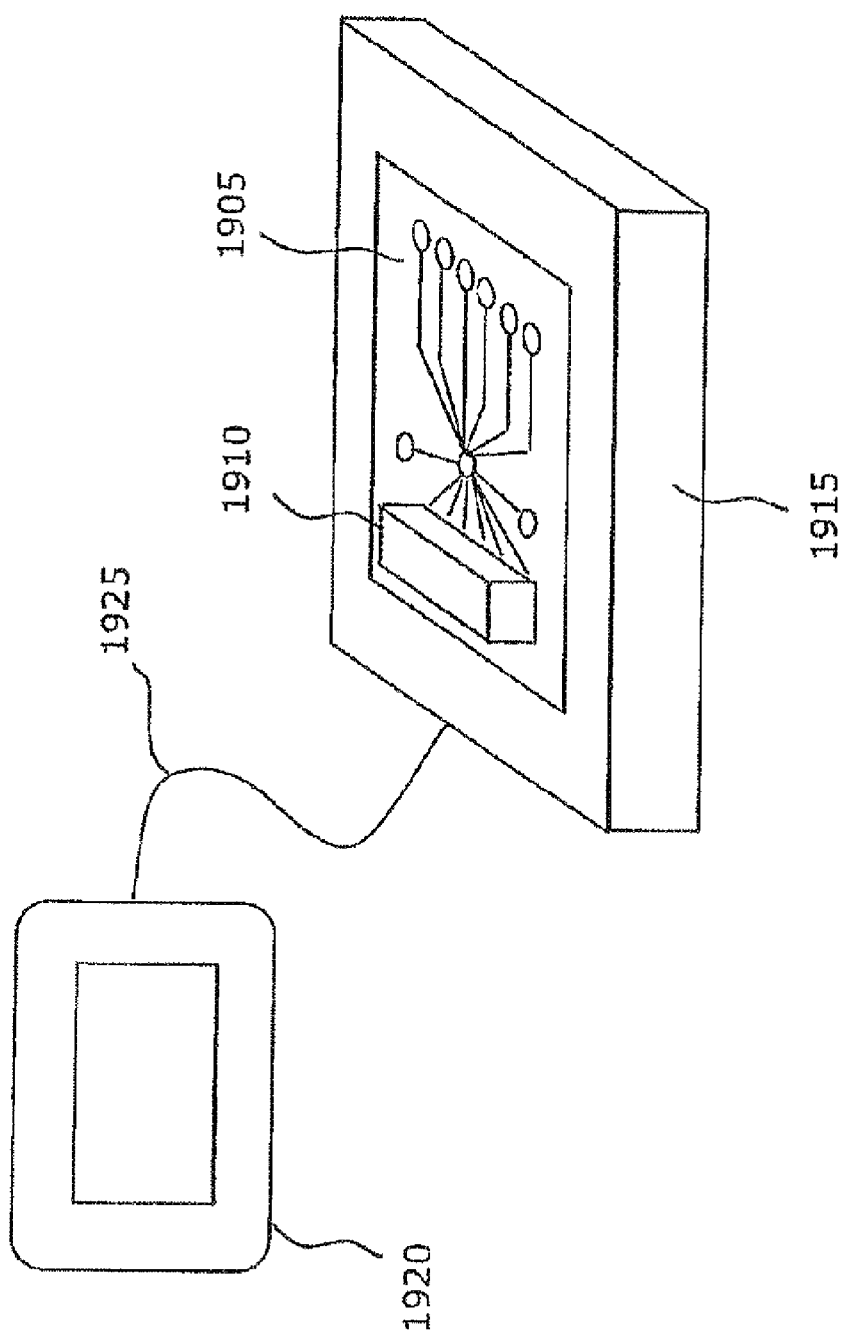
FIG. 18 shows a complete and self-contained microfluidic system including a computer, a controller and a chip.

FIG. 18 shows a complete system including an assay chip 1905, a cartridge 1910, a controller 1915, and a computer 1920. The controller 1915 allows for automated control of the various pump and valve structures of the chip 1905. In particular, the chip 1905 includes pneumatic drivers 1920 (not shown) positioned to be substantially aligned with the pump and valve structures of the chip 1905. Positive or negative pneumatic pressure is applied via the drivers 1920 in accordance with input signals provided through input wires 1925.

The computer 1920 may provide a user interface for controlling the controller 1915. A user may provide inputs specifying requirements on a particular assay run using a graphical user input provided by the computer 1920. The computer is electrically connected to the controller 1915 and provides signals to the controller 1915 so it acts in accordance with the user inputs.

Figure 19:
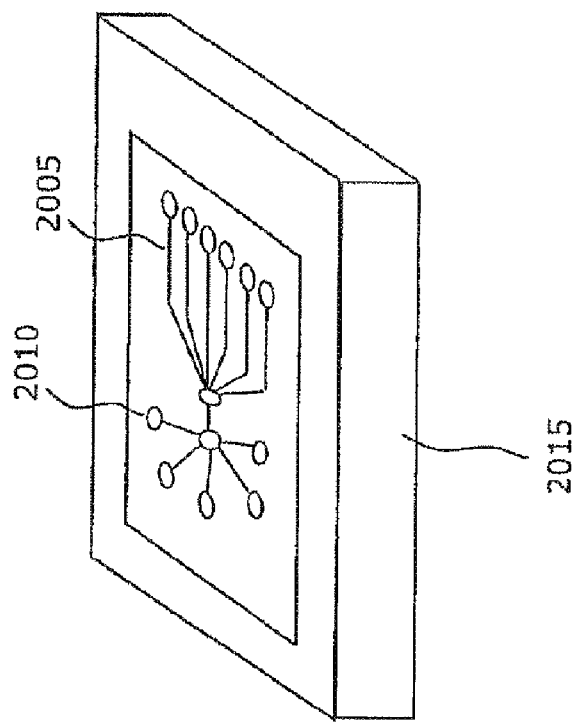
FIG. 19 illustrates an alternate embodiment of a chip coupled to a controller.

FIG. 19 illustrates an embodiment with an assay chip 2005 ducted to a separate reagent chip 2010 on a programmable controller 2015. The controller 2015 includes a group of pneumatic solenoid valves. Each of the pneumatic signals from the solenoid valves is routed through the chip to one or a series of microfluidic valves on a specific chip layout. For example, in one embodiment there is an individual solenoid valve connected to each of the corresponding reagent reservoirs 12 of FIG. 1, but all six of the channel pumps 44 are connected in parallel to a set of four solenoid valves so they may act together. There is a solenoid drive board in the controller 2015 that takes the signals from the computer and turns on the appropriate solenoid valve to actuate the required microfluidic valve. An electrical signal from the computer will cause a solenoid valve to switch from a normally pressurized state to a vacuum state. This opens the attached microfluidic valve. If a specific sequence of solenoid valve actuations is to be run repeatedly, the computer connection to the controller is not necessary. The microprocessor on the control board includes a memory which may store the sequence and thus an assay may be run independently of external computer control.

As mentioned above with respect to FIG. 1, the microfluidic chip of the invention generally includes a top substrate 7, a bottom substrate 6, and a membrane 8 disposed therebetween. The microfeatures (e.g., pumps, valves, or reservoirs) are fabricated in one or more of the top substrate 7, the bottom substrate 6, and the membrane 8. In certain methods of fabrication, the top substrate 7 and the membrane 8 are laminated together, and similarly the membrane 8 and the bottom substrate 6 are laminated together. While any lamination method known in the art may be used, in one aspect of the invention these layers are laminated by: 1) using a weak solvent bonding agent, and 2) laminating the layers under mild conditions, such as under low heat or low pressure. This is beneficial at least in part because this lamination method reduces or eliminates damage to the microfeatures during the lamination process. More particularly, in an exemplary use, the weak solvent bonding agent is applied to one or both surfaces to be adhered, and then mild pressure (e.g., from moderate heat or moderate physical pressure pressing the surfaces together) adheres the surfaces.

According to an aspect, the weak solvent bonding agent may be chemically defined as:

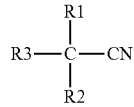

where, R1=H, OH or R, where R=alkyl, or is absent, R2=H, OH or R, where R=alkyl, or is absent, and R2=H, OH or R, where R=alkyl, or is absent.

Alternatively, the weak solvent may have a chemical formula of:

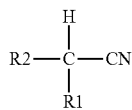

where R1=H, OH or R, where R=alkyl, or is absent, and R2=H, OH or R, where R=alkyl, or is absent.

Alternatively, the weak solvent may have a chemical formula of:

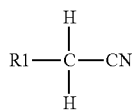

where R1=H, OH or R, where R=alkyl, or is absent.

In a particular aspect, the weak solvent bonding agent is acetonitrile. Acetonitrile is a versatile solvent that is widely used in analytical chemistry and other applications. It is 100% miscible with water and exhibits excellent optical properties. The ability of acetonitrile to have little or no effect on polymeric surfaces under ambient conditions but adhere the surfaces under moderate pressure makes it highly suitable for laminating polymeric materials such as polystyrene, polycarbonate, acrylic and other linear polymers. For example, microstructures disposed on a polystyrene substrate that was treated with acetonitrile at room temperature for at least several minutes did not exhibit any noticeable feature damage.

While some materials may be more susceptible to damage from acetonytrile than polystyrene, this increased susceptibility may be controlled by applying the acetonitrile at a lower temperature or, alternatively, by using a combination of acetonitrile and other inert solvents.

An additional benefit of acetonitrile-based lamination is that the process allows substrate alignment for structures containing multi-component layers or fluid networks constructed utilizing both a cover plate and a base plate. Unlike conventional strong solvent lamination, which tends to penetrate the polymeric surface and create a tacky bonding surface within seconds of solvent application, acetonitrile at room temperature may gently soften the surface. When two surfaces with acetonitrile disposed thereon are placed in contact at lower temperature prior to applying pressure, an operator may slide the two surfaces against each other to adjust their alignment. After aligning the surfaces, the operator may then apply pressure to the surfaces to laminate them together.

The foregoing description of the preferred embodiment of the invention has been presented for the purposes of illustration and description. It is not intended to be exhaustive or to limit the invention to the precise form disclosed. Many modifications and variations are possible in light of the teaching herein.

We claim:

1. A microfluidic device, comprising:
    a substrate having a plurality of channels disposed therein, each of the channels having an inlet end and an outlet end;
    a plurality of reservoirs of a type capable of holding a material, coupled to at least one of the inlet end and the outlet end of at least one of the plurality of channels;
    at least one bi-directional diaphragm pump comprising at least three non-elastomeric membrane-based valve structures;
    a distribution valve disposed in fluid coupling with the at least one reservoir and at least one of the inlet ends, wherein the distribution valve is adapted to controllably direct a flow of the material between at least two of the plurality of reservoirs via at least one of the channels coupled to the distribution valve; and
    at least one insert configured to inter-fit within at least one of the channels and having a reaction surface for interacting with the material, wherein the insert comprises a membrane.

2. The microfluidic device of claim 1, wherein the insert further comprises at least one membrane disk disposed over an aperture of an adhesive layer of the membrane.

3. The microfluidic device of claim 2, wherein the aperture is one of a circular shape and a shape comprising a circular region and two opposing rectangular regions open to the circular region.

4. The microfluidic device of claim 2, wherein the membrane disk is applied with at least one of a chemical agent and a biological agent.

5. The microfluidic device of claim 2, wherein the membrane disk is made from one of nitrocellulose, PVDF, polystyrene, and nylon.

* * * * *